US012805826B2

(12) United States Patent
Telfort et al.

(10) Patent No.: US 12,805,826 B2
(45) Date of Patent: Nov. 24, 2026

(54) ACOUSTIC RESPIRATORY MONITORING SYSTEMS AND METHODS

(71) Applicant: Masimo Corporation, Irvine, CA (US)

(72) Inventors: Valery G. Telfort, Irvine, CA (US); Mark Wylie, Dorval (CA)

(73) Assignee: Masimo Corporation, Irvine, CA (US)

( * ) Notice: Subject to any disclaimer, the term of this patent is extended or adjusted under 35 U.S.C. 154(b) by 1697 days.

(21) Appl. No.: 16/600,983

(22) Filed: Oct. 14, 2019

(65) Prior Publication Data

US 2020/0178923 A1 Jun. 11, 2020

Related U.S. Application Data

(63) Continuation of application No. 12/904,789, filed on Oct. 14, 2010, now Pat. No. 10,463,340.
(Continued)

(51) Int. Cl.
*A61B 5/00* (2006.01)
*A61B 5/08* (2006.01)
(Continued)

(52) U.S. Cl.
CPC .................................... *A61B 7/003* (2013.01)

(58) Field of Classification Search
CPC ......... A61B 7/003; A61B 7/04; A61B 5/0205; A61B 5/024; A61B 5/0816; A61B 5/113;
(Continued)

(56) References Cited

U.S. PATENT DOCUMENTS 2,699,465 A 1/1955 Selden
3,399,467 A 9/1968 Ravin
(Continued)

FOREIGN PATENT DOCUMENTS

CA 2490438 1/2004
CA 2262236 4/2008
(Continued)

OTHER PUBLICATIONS

US 8,740,816 B2, 06/2014, Telfort et al. (withdrawn)
(Continued)

*Primary Examiner* — Justin Xu
*Assistant Examiner* — Jonathan E. Cooper
(74) *Attorney, Agent, or Firm* — Knobbe, Martens, Olson & Bear, LLP

(57) ABSTRACT

An acoustic sensor is provided according to certain aspects for non-invasively detecting physiological acoustic vibrations indicative of one or more physiological parameters of a medical patient. The sensor can include an acoustic sensing element configured to generate a first signal in response to acoustic vibrations from a medical patient. The sensor can also include front-end circuitry configured to receive an input signal that is based at least in part on the first signal and to produce an amplified signal in response to the input signal. In some embodiments, the sensor further includes a compression module in communication with the front-end circuitry and configured to compress portions of at least one of the input signal and the amplified signal according to a first compression scheme, the compressed portions corresponding to portions of the first signal having a magnitude greater than a predetermined threshold level.

9 Claims, 15 Drawing Sheets

Related U.S. Application Data

(60) Provisional application No. 61/252,099, filed on Oct. 15, 2009.

(51) Int. Cl.
*A61B 7/00* (2006.01)
*A61B 7/04* (2006.01)
*H03G 7/00* (2006.01)
*H03G 7/08* (2006.01)
*A61B 5/0205* (2006.01)
*A61B 5/024* (2006.01)
*A61B 5/113* (2006.01)

(58) Field of Classification Search
CPC ... A61B 5/6833; A61B 5/7203; A61B 5/7232; A61B 2562/0204; A61B 17/2202; H03G 7/002; H03G 7/08; H03G 3/3005; H03G 1/04; H03G 3/301; H04R 17/00; H04R 19/04; H04R 19/005; H04R 25/356; H04R 25/505; B81B 2201/0257
USPC .................................. 600/529, 437; 128/901
See application file for complete search history.

(56) References Cited

U.S. PATENT DOCUMENTS 3,682,161 A 8/1972 Alibert
3,867,925 A 2/1975 Ersek
3,951,230 A 4/1976 Littmann
3,991,304 A 11/1976 Hillsman
4,127,749 A 11/1978 Atoji et al.
4,170,720 A * 10/1979 Killion ..................... H03G 7/08 381/381
4,254,302 A 3/1981 Walshe
4,326,143 A 4/1982 Guth et al.
4,381,788 A 5/1983 Douglas
4,401,125 A 8/1983 Taylor et al.
4,413,202 A 11/1983 Krempl et al.
4,474,185 A 10/1984 Diamond
4,499,905 A 2/1985 Greenberg
4,537,200 A 8/1985 Widrow
4,576,179 A 3/1986 Manus et al.
4,578,613 A 3/1986 Posthuma de Boer et al.
4,634,917 A 1/1987 Dvorksy et al.
4,653,498 A 3/1987 New, Jr. et al.
4,672,976 A 6/1987 Kroll
4,718,099 A * 1/1988 Hotvet ................. H04R 25/356 381/317
4,805,633 A 2/1989 Kotani et al.
4,827,943 A 5/1989 Bornn et al.
4,871,046 A 10/1989 Turner
4,884,809 A 12/1989 Rowan
4,924,876 A * 5/1990 Cameron .............. G01F 15/068 128/207.18
4,947,853 A 8/1990 Hon
4,947,859 A 8/1990 Brewer et al.
4,960,118 A 10/1990 Pennock
4,960,128 A 10/1990 Gordon et al.
4,964,408 A 10/1990 Hink et al.
4,982,738 A 1/1991 Griebel
4,995,473 A 2/1991 Packard
5,003,605 A 3/1991 Phillipps et al.
5,033,032 A 7/1991 Houghtaling
5,036,857 A 8/1991 Semmlow et al.
5,041,187 A 8/1991 Hink et al.
5,069,213 A 12/1991 Polczynski
5,078,151 A 1/1992 Laballery
5,140,992 A 8/1992 Zuckerwar et al.
5,143,078 A 9/1992 Mather et al.
5,163,438 A 11/1992 Gordon et al.
5,241,689 A * 8/1993 Schwed ................... H04B 1/64 455/72
5,269,314 A 12/1993 Kendall et al.
5,273,036 A 12/1993 Kronberg et al.
5,278,627 A 1/1994 Aoyagi et al.
5,319,355 A 6/1994 Russek
5,333,106 A 7/1994 Lanpher et al.
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
5,394,877 A 3/1995 Orr et al.
5,406,952 A 4/1995 Barnes et al.
D359,546 S 6/1995 Savage et al.
5,428,193 A 6/1995 Mandiberg
5,431,170 A 7/1995 Mathews
5,436,499 A 7/1995 Namavar et al.
D361,840 S 8/1995 Savage et al.
D362,063 S 9/1995 Savage et al.
5,448,996 A 9/1995 Bellin et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,539,831 A 7/1996 Harley
5,561,275 A 10/1996 Savage et al.
5,562,002 A 10/1996 Lalin
5,564,108 A 10/1996 Hunsaker et al.
5,566,671 A 10/1996 Lyons
5,578,799 A 11/1996 Callahan et al.
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,685,299 A 11/1997 Diab et al.
5,726,440 A 3/1998 Kalkhoran et al.
5,730,140 A 3/1998 Fitch
D393,830 S 4/1998 Tobler et al.
5,737,367 A 4/1998 Wuppermann
5,738,106 A 4/1998 Yamamori et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,812,678 A 9/1998 Scalise et al.
5,822,442 A * 10/1998 Agnew ................ H04R 25/356 330/278
5,823,950 A 10/1998 Diab et al.
5,825,895 A 10/1998 Grasfield et al.
5,830,131 A 11/1998 Caro et al.
5,833,618 A 11/1998 Caro et al.
5,860,919 A 1/1999 Kiani-Azarbayjany et al.
5,862,238 A * 1/1999 Agnew ................ H04R 25/356 381/108
5,890,929 A 4/1999 Mills et al.
5,904,654 A 5/1999 Wohltmann et al.
5,912,656 A 6/1999 Tham et al.
5,919,134 A 7/1999 Diab
5,921,941 A 7/1999 Longobardo et al.
5,934,925 A 8/1999 Tobler et al.
5,940,182 A 8/1999 Lepper, Jr. et al.
5,977,538 A 11/1999 Unger et al.
5,987,343 A 11/1999 Kinast
5,989,193 A 11/1999 Sullivan
5,995,855 A 11/1999 Kiani et al.
5,997,343 A 12/1999 Mills et al.
6,002,952 A 12/1999 Diab et al.

(56) References Cited

U.S. PATENT DOCUMENTS

| | | | |
|---|---|---|---|
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,048,323 | A | 4/2000 | Hon |
| 6,066,204 | A | 5/2000 | Haven |
| 6,067,462 | A | 5/2000 | Diab et al. |
| 6,081,735 | A | 6/2000 | Diab et al. |
| 6,083,156 | A | 7/2000 | Lisiecki |
| 6,088,607 | A | 7/2000 | Diab et al. |
| 6,091,973 | A | 7/2000 | Colla et al. |
| 6,106,481 | A | 8/2000 | Cohen |
| 6,110,522 | A | 8/2000 | Lepper, Jr. et al. |
| 6,115,673 | A | 9/2000 | Malin et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,168,568 | B1 | 1/2001 | Gavriely |
| 6,178,343 | B1 | 1/2001 | Bindszus et al. |
| 6,184,521 | B1 | 2/2001 | Coffin, IV et al. |
| 6,206,830 | B1 | 3/2001 | Diab et al. |
| 6,210,344 | B1 | 4/2001 | Perin et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,248,083 | B1 | 6/2001 | Smith et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,261,237 | B1 | 7/2001 | Swanson et al. |
| 6,261,238 | B1 | 7/2001 | Gavriely |
| 6,263,222 | B1 | 7/2001 | Diab et al. |
| 6,271,760 | B1 | 8/2001 | Watanabe et al. |
| 6,275,594 | B1 | 8/2001 | Senoo et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,295,365 | B1 | 9/2001 | Ota |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,014 | B1 | 6/2002 | Toda |
| 6,411,373 | B1 | 6/2002 | Garside et al. |
| 6,415,033 | B1 | 7/2002 | Halleck et al. |
| 6,415,167 | B1 | 7/2002 | Blank et al. |
| 6,423,013 | B1 | 7/2002 | Bakker et al. |
| 6,430,437 | B1 | 8/2002 | Marro |
| 6,430,525 | B1 | 8/2002 | Weber et al. |
| 6,438,238 | B1 | 8/2002 | Callahan |
| 6,463,311 | B1 | 10/2002 | Diab |
| 6,470,199 | B1 | 10/2002 | Kopotic et al. |
| 6,486,588 | B2 | 11/2002 | Doron et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,517,497 | B2 | 2/2003 | Rymut et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,560,470 | B1 | 5/2003 | Pologe |
| 6,571,113 | B1 | 5/2003 | Fein et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,702,755 | B1 | 3/2004 | Stasz et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,074 | B1 | 4/2004 | Kästle |
| 6,725,075 | B2 | 4/2004 | Al-Ali |
| 6,728,560 | B2 | 4/2004 | Kollias et al. |
| 6,735,459 | B2 | 5/2004 | Parker |
| 6,738,652 | B2 | 5/2004 | Mattu et al. |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,788,965 | B2 | 9/2004 | Ruchti et al. |
| 6,792,300 | B1 | 9/2004 | Diab et al. |
| 6,813,511 | B2 | 11/2004 | Diab et al. |
| 6,816,241 | B2 | 11/2004 | Grubisic |
| 6,816,741 | B2 | 11/2004 | Diab |
| 6,816,744 | B2 | 11/2004 | Garfield et al. |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,869,402 | B2 | 3/2005 | Arnold |
| 6,876,931 | B2 | 4/2005 | Lorenz et al. |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,937,736 | B2 | 8/2005 | Toda |
| 6,939,305 | B2 | 9/2005 | Flaherty et al. |
| 6,943,348 | B1 | 9/2005 | Coffin IV |
| 6,950,687 | B2 | 9/2005 | Al-Ali |
| 6,954,971 | B1 | 10/2005 | Bryant et al. |
| 6,956,649 | B2 | 10/2005 | Acosta et al. |
| 6,961,598 | B2 | 11/2005 | Diab |
| 6,970,792 | B1 | 11/2005 | Diab |
| 6,979,812 | B2 | 12/2005 | Al-Ali |

(56) References Cited

U.S. PATENT DOCUMENTS

| | | | |
|---|---|---|---|
| 6,985,764 | B2 | 1/2006 | Mason et al. |
| 6,990,364 | B2 | 1/2006 | Ruchti et al. |
| 6,993,371 | B2 | 1/2006 | Kiani et al. |
| 6,996,427 | B2 | 2/2006 | Ali et al. |
| 6,998,247 | B2 | 2/2006 | Monfre et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,020,508 | B2 | 3/2006 | Stivoric et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,035,684 | B2 | 4/2006 | Lee |
| 7,039,449 | B2 | 5/2006 | Ai-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,067,893 | B2 | 6/2006 | Mills et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| 7,096,060 | B2 | 8/2006 | Arand et al. |
| 7,110,804 | B2 | 9/2006 | Baumer et al. |
| D529,616 | S | 10/2006 | Deros et al. |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,190,945 | B1 | 3/2007 | Crisafulli |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,246,069 | B1 | 7/2007 | O'Hanlon et al. |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,270,126 | B2 | 9/2007 | Wallace et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,361,148 | B2 | 4/2008 | Narimatsu |
| 7,368,855 | B2 | 5/2008 | Orten |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al Ali et al. |
| 7,377,899 | B2 | 5/2008 | Weber et al. |
| 7,383,070 | B2 | 6/2008 | Diab et al. |
| 7,395,158 | B2 | 7/2008 | Monfre et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,457,757 | B1 * | 11/2008 | McNeill .............. G10L 21/0208<br>704/500 |
| 7,467,002 | B2 | 12/2008 | Weber et al. |
| 7,469,157 | B2 | 12/2008 | Diab et al. |
| 7,469,158 | B2 | 12/2008 | Cutler et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,515,044 | B2 | 4/2009 | Welch et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty |
| 7,620,674 | B2 | 11/2009 | Ruchti et al. |
| D606,659 | S | 12/2009 | Kiani et al. |
| 7,625,117 | B2 | 12/2009 | Haslett et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| 7,662,105 | B2 | 2/2010 | Hatlestad |
| 7,668,588 | B2 | 2/2010 | Kovacs |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,783,056 | B2 | 8/2010 | Wilmink |
| 7,791,155 | B2 | 9/2010 | Diab |
| 7,801,581 | B2 | 9/2010 | Diab |
| 7,806,226 | B2 | 10/2010 | Drummong et al. |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,860,553 | B2 | 12/2010 | Goveri et al. |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,903,825 | B1 * | 3/2011 | Melanson ................ H03G 3/32<br>381/103 |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |

(56) References Cited

U.S. PATENT DOCUMENTS

| | | | |
|---|---|---|---|
| 7,937,130 B2 | 5/2011 | Diab et al. | |
| 7,940,937 B2 | 5/2011 | Smith | |
| 7,941,199 B2 | 5/2011 | Kiani | |
| 7,951,086 B2 | 5/2011 | Flaherty et al. | |
| 7,957,780 B2 | 6/2011 | Lamego et al. | |
| 7,962,188 B2 | 6/2011 | Kiani et al. | |
| 7,962,190 B1 | 6/2011 | Diab et al. | |
| 7,976,472 B2 | 7/2011 | Kiani | |
| 7,976,480 B2 | 7/2011 | Grajales et al. | |
| 7,988,637 B2 | 8/2011 | Diab | |
| 7,988,688 B2 | 8/2011 | Webb et al. | |
| 7,990,382 B2 | 8/2011 | Kiani | |
| 7,991,165 B2 | 8/2011 | Kassal et al. | |
| 7,991,446 B2 | 8/2011 | Al-Ali et al. | |
| 8,000,761 B2 | 8/2011 | Al-Ali | |
| 8,008,088 B2 | 8/2011 | Bellott et al. | |
| RE42,753 E | 9/2011 | Kiani-Azarbayjany et al. | |
| 8,019,400 B2 | 9/2011 | Diab et al. | |
| 8,028,701 B2 | 10/2011 | Al-Ali et al. | |
| 8,029,765 B2 | 10/2011 | Bellott et al. | |
| 8,036,727 B2 | 10/2011 | Schurman et al. | |
| 8,036,728 B2 | 10/2011 | Diab et al. | |
| 8,046,040 B2 | 10/2011 | Ali et al. | |
| 8,046,041 B2 | 10/2011 | Diab et al. | |
| 8,046,042 B2 | 10/2011 | Diab et al. | |
| 8,048,040 B2 | 11/2011 | Kiani | |
| 8,050,728 B2 | 11/2011 | Al-Ali et al. | |
| 8,092,396 B2 | 1/2012 | Bagha et al. | |
| 8,108,039 B2 | 1/2012 | Saliga et al. | |
| RE43,169 E | 2/2012 | Parker | |
| 8,116,841 B2 | 2/2012 | Bly et al. | |
| 8,118,620 B2 | 2/2012 | Al-Ali et al. | |
| 8,121,673 B2 | 2/2012 | Tran | |
| 8,126,528 B2 | 2/2012 | Diab et al. | |
| 8,128,572 B2 | 3/2012 | Diab et al. | |
| 8,130,105 B2 | 3/2012 | Al-Ali et al. | |
| 8,145,287 B2 | 3/2012 | Diab et al. | |
| 8,150,487 B2 | 4/2012 | Diab et al. | |
| 8,175,672 B2 | 5/2012 | Parker | |
| 8,180,420 B2 | 5/2012 | Diab et al. | |
| 8,182,443 B1 | 5/2012 | Kiani | |
| 8,185,180 B2 | 5/2012 | Diab et al. | |
| 8,190,223 B2 | 5/2012 | Al-Ali et al. | |
| 8,190,227 B2 | 5/2012 | Diab et al. | |
| 8,203,438 B2 | 6/2012 | Kiani et al. | |
| 8,203,704 B2 | 6/2012 | Merritt et al. | |
| 8,204,566 B2 | 6/2012 | Schurman et al. | |
| 8,214,007 B2 | 7/2012 | Baker et al. | |
| 8,219,172 B2 | 7/2012 | Schurman et al. | |
| 8,224,411 B2 | 7/2012 | Al-Ali et al. | |
| 8,228,181 B2 | 7/2012 | Al-Ali et al. | |
| 8,229,532 B2 | 7/2012 | Davis | |
| 8,229,533 B2 | 7/2012 | Diab et al. | |
| 8,233,955 B2 | 7/2012 | Al-Ali et al. | |
| 8,241,223 B2 | 8/2012 | Gavriely et al. | |
| 8,244,325 B2 | 8/2012 | Al-Ali et al. | |
| 8,255,026 B1 | 8/2012 | Al-Ali | |
| 8,255,027 B2 | 8/2012 | Al-Ali et al. | |
| 8,255,028 B2 | 8/2012 | Al-Ali et al. | |
| 8,260,577 B2 | 9/2012 | Weber et al. | |
| 8,265,291 B2 | 9/2012 | Bridger et al. | |
| 8,265,723 B1 | 9/2012 | McHale et al. | |
| 8,274,360 B2 | 9/2012 | Sampath et al. | |
| 8,275,140 B2 | 9/2012 | Smith | |
| 8,280,473 B2 | 10/2012 | Al-Ali | |
| 8,301,217 B2 | 10/2012 | Al-Ali et al. | |
| 8,306,596 B2 | 11/2012 | Schurman et al. | |
| 8,310,336 B2 | 11/2012 | Muhsin et al. | |
| 8,315,683 B2 | 11/2012 | Al-Ali et al. | |
| 8,320,576 B1 | 11/2012 | Abbruscato | |
| RE43,860 E | 12/2012 | Parker | |
| 8,337,403 B2 | 12/2012 | Al-Ali et al. | |
| 8,346,330 B2 | 1/2013 | Lamego | |
| 8,352,052 B1 * | 1/2013 | Green ...................... | H03G 3/10 700/94 |
| 8,353,842 B2 | 1/2013 | Al-Ali et al. | |
| 8,355,766 B2 | 1/2013 | MacNeish, III et al. | |
| 8,359,080 B2 | 1/2013 | Diab et al. | |
| 8,364,223 B2 | 1/2013 | Al-Ali et al. | |
| 8,364,226 B2 | 1/2013 | Diab et al. | |
| 8,374,665 B2 | 2/2013 | Lamego | |
| 8,385,995 B2 | 2/2013 | Al-ali et al. | |
| 8,385,996 B2 | 2/2013 | Smith et al. | |
| 8,388,353 B2 | 3/2013 | Kiani et al. | |
| 8,396,228 B2 | 3/2013 | Bilan | |
| 8,399,822 B2 | 3/2013 | Al-Ali | |
| 8,401,602 B2 | 3/2013 | Kiani | |
| 8,403,865 B2 | 3/2013 | Halperin et al. | |
| 8,405,608 B2 | 3/2013 | Al-Ali et al. | |
| 8,414,499 B2 | 4/2013 | Al-ali et al. | |
| 8,418,524 B2 | 4/2013 | Ai-Ali | |
| 8,423,106 B2 | 4/2013 | Lamego et al. | |
| 8,428,967 B2 | 4/2013 | Olsen et al. | |
| 8,430,817 B1 | 4/2013 | Al-Ali et al. | |
| 8,437,825 B2 | 5/2013 | Dalvi et al. | |
| 8,449,469 B2 | 5/2013 | Banet et al. | |
| 8,455,290 B2 | 6/2013 | Siskavich | |
| 8,457,703 B2 | 6/2013 | Al-Ali | |
| 8,457,707 B2 | 6/2013 | Kiani | |
| 8,463,349 B2 | 6/2013 | Diab et al. | |
| 8,466,286 B2 | 6/2013 | Bellot et al. | |
| 8,471,713 B2 | 6/2013 | Poeze et al. | |
| 8,473,020 B2 | 6/2013 | Kiani et al. | |
| 8,483,787 B2 | 7/2013 | Al-Ali et al. | |
| 8,489,364 B2 | 7/2013 | Weber et al. | |
| 8,491,489 B2 | 7/2013 | Shin et al. | |
| 8,498,684 B2 | 7/2013 | Weber et al. | |
| 8,504,128 B2 | 8/2013 | Blank et al. | |
| 8,509,867 B2 | 8/2013 | Workman et al. | |
| 8,515,509 B2 | 8/2013 | Bruinsma et al. | |
| 8,517,981 B2 | 8/2013 | Zornow | |
| 8,523,781 B2 | 9/2013 | Ai-Ali | |
| 8,526,665 B2 | 9/2013 | Lutz et al. | |
| 8,529,301 B2 | 9/2013 | Al-Ali et al. | |
| 8,532,727 B2 | 9/2013 | Ali et al. | |
| 8,532,728 B2 | 9/2013 | Diab et al. | |
| D692,145 S | 10/2013 | Al-Ali et al. | |
| 8,547,209 B2 | 10/2013 | Kiani et al. | |
| 8,548,548 B2 | 10/2013 | Al-Ali | |
| 8,548,549 B2 | 10/2013 | Schurman et al. | |
| 8,548,550 B2 | 10/2013 | Al-Ali et al. | |
| 8,560,032 B2 | 10/2013 | Al-Ali et al. | |
| 8,560,034 B1 | 10/2013 | Diab et al. | |
| 8,570,167 B2 | 10/2013 | Al-Ali | |
| 8,570,503 B2 | 10/2013 | Vo et al. | |
| 8,571,617 B2 | 10/2013 | Reichgott et al. | |
| 8,571,618 B1 | 10/2013 | Lamego et al. | |
| 8,571,619 B2 | 10/2013 | Al-Ali et al. | |
| 8,577,431 B2 | 11/2013 | Lamego et al. | |
| 8,581,732 B2 | 11/2013 | Al-Ali et al. | |
| 8,584,345 B2 | 11/2013 | Al-Ali et al. | |
| 8,588,880 B2 | 11/2013 | Abdul-Hafiz et al. | |
| 8,600,467 B2 | 12/2013 | Al-Ali et al. | |
| 8,606,342 B2 | 12/2013 | Diab | |
| 8,626,255 B2 | 1/2014 | Al-Ali et al. | |
| 8,630,691 B2 | 1/2014 | Lamego et al. | |
| 8,634,889 B2 | 1/2014 | Al-Ali et al. | |
| 8,641,595 B2 | 2/2014 | Basinger | |
| 8,641,631 B2 | 2/2014 | Sierra et al. | |
| 8,652,060 B2 | 2/2014 | Al-Ali et al. | |
| 8,663,107 B2 | 3/2014 | Kiani | |
| 8,666,468 B1 | 3/2014 | Ai-Ali | |
| 8,667,967 B2 | 3/2014 | Al-Ali et al. | |
| 8,670,811 B2 | 3/2014 | O'Reilly | |
| 8,670,814 B2 | 3/2014 | Diab et al. | |
| 8,676,286 B2 | 3/2014 | Weber et al. | |
| 8,682,407 B2 | 3/2014 | Al-Ali | |
| RE44,823 E | 4/2014 | Parker | |
| RE44,875 E | 4/2014 | Kiani et al. | |
| 8,688,183 B2 | 4/2014 | Bruinsma et al. | |
| 8,688,189 B2 | 4/2014 | Shennib | |
| 8,690,799 B2 | 4/2014 | Telfort et al. | |
| 8,700,112 B2 | 4/2014 | Kiani | |
| 8,702,627 B2 | 4/2014 | Telfort et al. | |

(56) References Cited

U.S. PATENT DOCUMENTS

| | | | |
|---|---|---|---|
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiana |
| 8,740,792 | B1 | 6/2014 | Kiana et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali et al. |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Ai-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,961,413 | B2 | 2/2015 | Teller et al. |
| 8,965,471 | B2 | 2/2015 | Ego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Ai-Ali |
| 9,113,832 | B2 | 8/2015 | Ai-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Ai-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,411,936 | B2 | 8/2016 | Landrum et al. |
| 9,436,645 | B2 | 9/2016 | Al-Ali et al. |
| 9,439,599 | B2 | 9/2016 | Thompson et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,692 | B2 | 4/2017 | Lamego et al. |
| 9,622,693 | B2 | 4/2017 | Diab |
| D788,312 | S | 5/2017 | Al-Ali et al. |
| 9,636,055 | B2 | 5/2017 | Al-Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |

(56) References Cited

U.S. PATENT DOCUMENTS

| | | | |
|---|---|---|---|
| 9,668,703 | B2 | 6/2017 | Al-Ali |
| 9,675,286 | B2 | 6/2017 | Diab |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,717,425 | B2 | 8/2017 | Kiani et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| 9,750,442 | B2 | 9/2017 | Olsen |
| 9,750,443 | B2 | 9/2017 | Smith et al. |
| 9,750,461 | B1 | 9/2017 | Telfort |
| 9,775,545 | B2 | 10/2017 | Al-Ali et al. |
| 9,775,546 | B2 | 10/2017 | Diab et al. |
| 9,775,570 | B2 | 10/2017 | Al-Ali |
| 9,778,079 | B1 | 10/2017 | Al-Ali et al. |
| 9,782,077 | B2 | 10/2017 | Lamego et al. |
| 9,782,110 | B2 | 10/2017 | Kiani et al. |
| 9,787,568 | B2 | 10/2017 | Lamego et al. |
| 9,788,735 | B2 | 10/2017 | Al-Ali |
| 9,788,768 | B2 | 10/2017 | Al-Ali et al. |
| 9,795,300 | B2 | 10/2017 | Al-Ali |
| 9,795,310 | B2 | 10/2017 | Al-Ali |
| 9,795,358 | B2 | 10/2017 | Telfort et al. |
| 9,795,739 | B2 | 10/2017 | Al-Ali et al. |
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| 9,833,152 | B2 | 12/2017 | Kiani et al. |
| 9,833,180 | B2 | 12/2017 | Shakespeare et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Al-Ali et al. |
| 9,848,807 | B2 | 12/2017 | Lamego |
| 9,861,298 | B2 | 1/2018 | Eckerbom et al. |
| 9,861,304 | B2 | 1/2018 | Al-Ali et al. |
| 9,861,305 | B1 | 1/2018 | Weber et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| 9,891,079 | B2 | 2/2018 | Dalvi |
| 9,895,107 | B2 | 2/2018 | Al-Ali et al. |
| 9,924,893 | B2 | 3/2018 | Schurman et al. |
| 9,924,897 | B1 | 3/2018 | Abdul-Hafiz |
| 9,936,917 | B2 | 4/2018 | Poeze et al. |
| 9,955,937 | B2 | 5/2018 | Telfort et al. |
| 9,965,946 | B2 | 5/2018 | Al-Ali et al. |
| 9,968,266 | B2 | 5/2018 | An et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,098,610 | B2 | 10/2018 | Al-Ali et al. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Ai-Ali |
| 10,342,497 | B2 | 7/2019 | Burgin et al. |
| 10,349,895 | B2 | 7/2019 | Telfort et al. |
| 10,357,209 | B2 | 7/2019 | Al-Al |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| RE47,882 | E | 3/2020 | Al-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |

(56) References Cited

U.S. PATENT DOCUMENTS

| | | | |
|---|---|---|---|
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Ai-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |
| 12,495,967 | B2 | 12/2025 | Muhsin et al. |
| 12,495,999 | B2 | 12/2025 | Al-Ali et al. |
| 12,507,952 | B2 | 12/2025 | Al-Ali et al. |
| 12,521,021 | B2 | 1/2026 | Al-Ali et al. |
| 12,521,506 | B2 | 1/2026 | Yu et al. |
| 12,538,084 | B1 | 1/2026 | Telfort et al. |
| 12,539,046 | B2 | 2/2026 | Kiani |
| D1,119,639 | S | 3/2026 | Al-Ali et al. |
| 12,575,797 | B2 | 3/2026 | Olsen et al. |
| D1,124,008 | S | 4/2026 | Indorf et al. |
| D1,124,017 | S | 4/2026 | Indorf et al. |
| D1,124,917 | S | 5/2026 | Al-Ali et al. |
| 12,616,623 | B1 | 5/2026 | Al-Ali et al. |
| 2001/0034477 | A1 | 10/2001 | Mansfield et al. |
| 2001/0039483 | A1 | 11/2001 | Brand et al. |

(56) References Cited

U.S. PATENT DOCUMENTS

2002/0010401 A1 1/2002 Bushmakin et al.
2002/0058864 A1 5/2002 Mansfield et al.
2002/0133080 A1 9/2002 Apruzzese et al.
2002/0193670 A1 12/2002 Garfield et al.
2003/0013975 A1 1/2003 Kiani
2003/0018243 A1 1/2003 Gerhardt et al.
2003/0135087 A1 7/2003 Hickle et al.
2003/0144582 A1 7/2003 Cohen et al.
2003/0149349 A1 8/2003 Jensen
2003/0156288 A1 8/2003 Barnum et al.
2003/0196660 A1 10/2003 Haveri
2003/0212312 A1 11/2003 Coffin, IV et al.
2004/0015093 A1 1/2004 Knapp, II et al.
2004/0106163 A1 6/2004 Workman, Jr. et al.
2004/0149282 A1 8/2004 Hickle
2004/0158162 A1 8/2004 Narimatsu
2004/0167416 A1 8/2004 Lee
2004/0215094 A1 10/2004 Baumer et al.
2004/0226771 A1 11/2004 Werblud
2004/0228494 A1 11/2004 Smith
2004/0243016 A1 12/2004 Sanderson
2005/0033128 A1 2/2005 Ali
2005/0055276 A1 3/2005 Kiani et al.
2005/0065417 A1 3/2005 Ali
2005/0114455 A1 5/2005 Conroy et al.
2005/0123071 A1 6/2005 Okada
2005/0234317 A1 10/2005 Kiani
2005/0283059 A1 12/2005 Vijay et al.
2006/0047215 A1 3/2006 Newman et al.
2006/0059324 A1 3/2006 Simske et al.
2006/0073719 A1 4/2006 Kiani
2006/0094943 A1 5/2006 Van Slyke
2006/0144397 A1 7/2006 Wallace et al.
2006/0155167 A1 7/2006 Elliott
2006/0161054 A1 7/2006 Reuss et al.
2006/0184052 A1 8/2006 Iwasawa
2006/0189871 A1 8/2006 Al-Ali et al.
2006/0190051 A1 8/2006 Gerber et al.
2006/0198533 A1 9/2006 Wang
2006/0238333 A1 10/2006 Welch et al.
2006/0264767 A1 11/2006 Shennib
2007/0016030 A1 1/2007 Stringer
2007/0049837 A1 3/2007 Shertukde et al.
2007/0056582 A1 3/2007 Wood et al.
2007/0058818 A1 3/2007 Yoshimine
2007/0073116 A1 3/2007 Kiani et al.
2007/0106179 A1 5/2007 Bagha et al.
2007/0118054 A1 5/2007 Pinhas
2007/0135725 A1 6/2007 Hatlestad
2007/0147639 A1* 6/2007 Richardson .............. H03G 1/04 381/107
2007/0165872 A1 7/2007 Bridger et al.
2007/0167855 A1 7/2007 Shin et al.
2007/0173730 A1 7/2007 Bikko
2007/0180140 A1 8/2007 Welch et al.
2007/0185397 A1 8/2007 Govari et al.
2007/0208262 A1 9/2007 Kovacs
2007/0208267 A1 9/2007 Schmid
2007/0244377 A1 10/2007 Cozad et al.
2007/0255153 A1 11/2007 Kumar et al.
2007/0282174 A1 12/2007 Sabatino
2007/0282478 A1 12/2007 Al-Ali et al.
2008/0039735 A1 2/2008 Hickerson
2008/0064965 A1 3/2008 Jay et al.
2008/0076972 A1 3/2008 Dorogusker et al.
2008/0077026 A1 3/2008 Banet et al.
2008/0077198 A1 3/2008 Webb et al.
2008/0077435 A1 3/2008 Muradia
2008/0093157 A1 4/2008 Drummond et al.
2008/0094228 A1 4/2008 Welch et al.
2008/0097249 A1 4/2008 Pool et al.
2008/0103375 A1 5/2008 Kiani
2008/0114220 A1 5/2008 Banet et al.
2008/0137876 A1 6/2008 Kassal et al.
2008/0139953 A1 6/2008 Baker et al.
2008/0143496 A1 6/2008 Linjama
2008/0162123 A1* 7/2008 Goldin ................ G10L 19/0204 704/226
2008/0188733 A1 8/2008 Al-Ali et al.
2008/0188760 A1 8/2008 Al-Ali
2008/0219464 A1 9/2008 Smith
2008/0221418 A1 9/2008 Al-Ali et al.
2008/0251313 A1 10/2008 Knight et al.
2008/0281219 A1 11/2008 Glickman et al.
2008/0310652 A1* 12/2008 Gustavsson .............. H03G 7/00 381/106
2009/0018409 A1 1/2009 Banet et al.
2009/0018429 A1 1/2009 Saliga et al.
2009/0036759 A1 2/2009 Ault et al.
2009/0076363 A1 3/2009 Bly et al.
2009/0093687 A1* 4/2009 Telfort ................ A61B 5/0215 600/300
2009/0095926 A1 4/2009 MacNeish, III
2009/0170664 A1 7/2009 Shirasaki
2009/0187065 A1 7/2009 Basinger
2009/0247924 A1 10/2009 Lamego et al.
2009/0247984 A1 10/2009 Lamego et al.
2009/0275813 A1 11/2009 Davis
2009/0275844 A1 11/2009 Al-Ali
2009/0299157 A1 12/2009 Telfort et al.
2009/0299742 A1* 12/2009 Toman ................ G10L 21/0208 704/E15.039
2009/0316925 A1 12/2009 Eisenfeld et al.
2010/0004518 A1 1/2010 Vo et al.
2010/0030040 A1 2/2010 Poeze et al.
2010/0069725 A1 3/2010 Al-Ali
2010/0090901 A1 4/2010 Smith et al.
2010/0094096 A1 4/2010 Petruzzelli et al.
2010/0099964 A1 4/2010 O'Reilly et al.
2010/0179438 A1 7/2010 Heneghan
2010/0195864 A1 8/2010 Lutz et al.
2010/0196861 A1* 8/2010 Lunner ................ H04R 25/505 434/112
2010/0204996 A1 8/2010 Zeng et al.
2010/0232615 A1 9/2010 Sörlander et al.
2010/0234718 A1 9/2010 Sampath et al.
2010/0256505 A1 10/2010 Xu
2010/0261979 A1 10/2010 Kiani
2010/0270257 A1 10/2010 Wachman et al.
2010/0305416 A1 12/2010 Bédard et al.
2010/0317936 A1 12/2010 Al-Ali et al.
2011/0001605 A1 1/2011 Kiani et al.
2011/0028802 A1 2/2011 Addison
2011/0028806 A1 2/2011 Merritt et al.
2011/0028809 A1 2/2011 Goodman
2011/0034831 A1 2/2011 Christensen et al.
2011/0040197 A1 2/2011 Welch et al.
2011/0066062 A1 3/2011 Banet et al.
2011/0082711 A1 4/2011 Poeze et al.
2011/0087081 A1 4/2011 Kiani et al.
2011/0087083 A1 4/2011 Poeze et al.
2011/0105854 A1 5/2011 Kiani et al.
2011/0118561 A1 5/2011 Tari et al.
2011/0125060 A1 5/2011 Telfort et al.
2011/0137297 A1 6/2011 Kiani et al.
2011/0172498 A1 7/2011 Olsen et al.
2011/0172967 A1 7/2011 Al-Ali et al.
2011/0196211 A1 8/2011 Al-Ali
2011/0208015 A1 8/2011 Welch et al.
2011/0209915 A1 9/2011 Fechter et al.
2011/0213212 A1 9/2011 Al-Ali
2011/0230733 A1 9/2011 Al-Ali
2011/0237911 A1 9/2011 Lamego et al.
2011/0237969 A1 9/2011 Eckerbom et al.
2011/0279963 A1 11/2011 Kumar et al.
2011/0288383 A1 11/2011 Diab
2011/0288431 A1 11/2011 Alshaer et al.
2011/0301444 A1 12/2011 Al-Ali
2012/0041316 A1 2/2012 Al-Ali et al.
2012/0046557 A1 2/2012 Kiani
2012/0059267 A1 3/2012 Lamego et al.
2012/0088984 A1 4/2012 Al-Ali et al.
2012/0116175 A1 5/2012 Al-Ali et al.
2012/0123231 A1 5/2012 O'Reilly

(56) References Cited

U.S. PATENT DOCUMENTS

| | | | |
|---|---|---|---|
| 2012/0165629 | A1 | 6/2012 | Merritt et al. |
| 2012/0179006 | A1 | 7/2012 | Jansen et al. |
| 2012/0209082 | A1 | 8/2012 | Al-Ali |
| 2012/0209084 | A1 | 8/2012 | Olsen et al. |
| 2012/0226117 | A1 | 9/2012 | Lamego et al. |
| 2012/0227739 | A1 | 9/2012 | Kiani |
| 2012/0230523 | A1 | 9/2012 | Ehrlund |
| 2012/0232427 | A1 | 9/2012 | Bakema et al. |
| 2012/0265039 | A1 | 10/2012 | Kiani |
| 2012/0283524 | A1 | 11/2012 | Kiani et al. |
| 2012/0286955 | A1 | 11/2012 | Welch et al. |
| 2012/0296178 | A1 | 11/2012 | Lamego et al. |
| 2012/0302920 | A1 | 11/2012 | Bridger et al. |
| 2012/0319816 | A1 | 12/2012 | Al-Ali |
| 2012/0330112 | A1 | 12/2012 | Lamego et al. |
| 2013/0023775 | A1 | 1/2013 | Lamego et al. |
| 2013/0041591 | A1 | 2/2013 | Lamego |
| 2013/0045685 | A1 | 2/2013 | Kiani |
| 2013/0046204 | A1 | 2/2013 | Lamego et al. |
| 2013/0060108 | A1 | 3/2013 | Schurman et al. |
| 2013/0060147 | A1 | 3/2013 | Welch et al. |
| 2013/0079610 | A1 | 3/2013 | Al-Ali |
| 2013/0090567 | A1 | 4/2013 | Al-Ali et al. |
| 2013/0096405 | A1 | 4/2013 | Garfio |
| 2013/0096936 | A1 | 4/2013 | Sampath et al. |
| 2013/0109935 | A1 | 5/2013 | Al-Ali et al. |
| 2013/0116578 | A1 | 5/2013 | An et al. |
| 2013/0162433 | A1 | 6/2013 | Muhsin et al. |
| 2013/0178749 | A1 | 7/2013 | Lamego |
| 2013/0190581 | A1 | 7/2013 | Al-Ali et al. |
| 2013/0197328 | A1 | 8/2013 | Diab et al. |
| 2013/0211214 | A1 | 8/2013 | Olsen |
| 2013/0243021 | A1 | 9/2013 | Siskavich |
| 2013/0253334 | A1 | 9/2013 | Al-Ali et al. |
| 2013/0261625 | A1 | 10/2013 | Koch |
| 2013/0262730 | A1 | 10/2013 | Al-Ali et al. |
| 2013/0267804 | A1 | 10/2013 | Al-Ali |
| 2013/0274571 | A1 | 10/2013 | Diab et al. |
| 2013/0274572 | A1 | 10/2013 | Al-Ali et al. |
| 2013/0296672 | A1 | 11/2013 | O'Neil et al. |
| 2013/0296713 | A1 | 11/2013 | Al-Ali et al. |
| 2013/0317327 | A1 | 11/2013 | Al-Ali et al. |
| 2013/0317370 | A1 | 11/2013 | Dalvi et al. |
| 2013/0324808 | A1 | 12/2013 | Al-Ali et al. |
| 2013/0324817 | A1 | 12/2013 | Diab |
| 2013/0331660 | A1 | 12/2013 | Al-Ali et al. |
| 2013/0331670 | A1 | 12/2013 | Kiani |
| 2013/0338461 | A1 | 12/2013 | Lamego et al. |
| 2013/0345921 | A1 | 12/2013 | Al-Ali et al. |
| 2014/0012100 | A1 | 1/2014 | Al-Ali et al. |
| 2014/0025306 | A1 | 1/2014 | Weber et al. |
| 2014/0034353 | A1 | 2/2014 | Al-Ali et al. |
| 2014/0051952 | A1 | 2/2014 | Reichgott et al. |
| 2014/0051953 | A1 | 2/2014 | Lamego et al. |
| 2014/0051954 | A1 | 2/2014 | Al-Ali et al. |
| 2014/0058230 | A1 | 2/2014 | Abdul-Hafiz et al. |
| 2014/0066783 | A1 | 3/2014 | Kiani et al. |
| 2014/0077956 | A1 | 3/2014 | Sampath et al. |
| 2014/0081097 | A1 | 3/2014 | Al-Ali et al. |
| 2014/0081100 | A1 | 3/2014 | Muhsin et al. |
| 2014/0094667 | A1 | 4/2014 | Schurman et al. |
| 2014/0100434 | A1 | 4/2014 | Diab et al. |
| 2014/0114199 | A1 | 4/2014 | Lamego et al. |
| 2014/0120564 | A1 | 5/2014 | Workman et al. |
| 2014/0121482 | A1 | 5/2014 | Merritt et al. |
| 2014/0121483 | A1 | 5/2014 | Kiani |
| 2014/0125495 | A1 | 5/2014 | Al-Ali |
| 2014/0127137 | A1 | 5/2014 | Bellott et al. |
| 2014/0128696 | A1 | 5/2014 | Al-Ali |
| 2014/0128699 | A1 | 5/2014 | Al-Ali et al. |
| 2014/0129702 | A1 | 5/2014 | Lamego et al. |
| 2014/0135588 | A1 | 5/2014 | Al-Ali et al. |
| 2014/0142399 | A1 | 5/2014 | Al-Ali et al. |
| 2014/0142401 | A1 | 5/2014 | Al-Ali et al. |
| 2014/0142402 | A1 | 5/2014 | Al-Ali et al. |
| 2014/0163344 | A1 | 6/2014 | Al-Ali |
| 2014/0163402 | A1 | 6/2014 | Lamego et al. |
| 2014/0166076 | A1 | 6/2014 | Kiani et al. |
| 2014/0171763 | A1 | 6/2014 | Diab |
| 2014/0180038 | A1 | 6/2014 | Kiani |
| 2014/0180154 | A1 | 6/2014 | Sierra et al. |
| 2014/0180160 | A1 | 6/2014 | Brown et al. |
| 2014/0187973 | A1 | 7/2014 | Brown et al. |
| 2014/0194709 | A1 | 7/2014 | Al-Ali et al. |
| 2014/0194711 | A1 | 7/2014 | Al-Ali |
| 2014/0194766 | A1 | 7/2014 | Al-Ali et al. |
| 2014/0200420 | A1 | 7/2014 | Al-Ali |
| 2014/0200422 | A1 | 7/2014 | Weber et al. |
| 2014/0206963 | A1 | 7/2014 | Al-Ali |
| 2014/0213864 | A1 | 7/2014 | Abdul-Hafiz et al. |
| 2014/0243627 | A1 | 8/2014 | Diab et al. |
| 2014/0266790 | A1 | 9/2014 | Al-Ali et al. |
| 2014/0275808 | A1 | 9/2014 | Poeze et al. |
| 2014/0275835 | A1 | 9/2014 | Lamego et al. |
| 2014/0275871 | A1 | 9/2014 | Lamego et al. |
| 2014/0275872 | A1 | 9/2014 | Merritt et al. |
| 2014/0275881 | A1 | 9/2014 | Lamego et al. |
| 2014/0276115 | A1 | 9/2014 | Dalvi et al. |
| 2014/0288400 | A1 | 9/2014 | Diab et al. |
| 2014/0309506 | A1 | 10/2014 | Lamego et al. |
| 2014/0316217 | A1 | 10/2014 | Purdon et al. |
| 2014/0316218 | A1 | 10/2014 | Purdon et al. |
| 2014/0316228 | A1 | 10/2014 | Blank et al. |
| 2014/0323825 | A1 | 10/2014 | Al-Ali et al. |
| 2014/0323897 | A1 | 10/2014 | Brown et al. |
| 2014/0323898 | A1 | 10/2014 | Purdon et al. |
| 2014/0330092 | A1 | 11/2014 | Al-Ali et al. |
| 2014/0330098 | A1 | 11/2014 | Merritt et al. |
| 2014/0330099 | A1 | 11/2014 | Al-Ali et al. |
| 2014/0333440 | A1 | 11/2014 | Kiana |
| 2014/0336481 | A1 | 11/2014 | Shakespeare et al. |
| 2014/0343436 | A1 | 11/2014 | Kiani |
| 2014/0357966 | A1 | 12/2014 | Al-Ali et al. |
| 2014/0371548 | A1 | 12/2014 | Al-Ali et al. |
| 2014/0378784 | A1 | 12/2014 | Kiani et al. |
| 2015/0005600 | A1 | 1/2015 | Blank et al. |
| 2015/0011907 | A1 | 1/2015 | Purdon et al. |
| 2015/0012231 | A1 | 1/2015 | Poeze et al. |
| 2015/0018650 | A1 | 1/2015 | Al-Ali et al. |
| 2015/0025406 | A1 | 1/2015 | Al-Ali |
| 2015/0032029 | A1 | 1/2015 | Al-Ali et al. |
| 2015/0038859 | A1 | 2/2015 | Dalvi |
| 2015/0045637 | A1 | 2/2015 | Dalvi |
| 2015/0051462 | A1 | 2/2015 | Olsen |
| 2015/0073241 | A1 | 3/2015 | Lamego |
| 2015/0080754 | A1 | 3/2015 | Purdon et al. |
| 2015/0087936 | A1 | 3/2015 | Al-Ali et al. |
| 2015/0094546 | A1 | 4/2015 | Al-Ali |
| 2015/0097701 | A1 | 4/2015 | Al-Ali et al. |
| 2015/0099950 | A1 | 4/2015 | Al-Ali et al. |
| 2015/0099951 | A1 | 4/2015 | Al-Ali et al. |
| 2015/0099955 | A1 | 4/2015 | Al-Ali et al. |
| 2015/0099998 | A1 | 4/2015 | Christensen et al. |
| 2015/0101844 | A1 | 4/2015 | Al-Ali et al. |
| 2015/0106121 | A1 | 4/2015 | Muhsin et al. |
| 2015/0112151 | A1 | 4/2015 | Muhsin et al. |
| 2015/0116076 | A1 | 4/2015 | Al-Ali et al. |
| 2015/0126830 | A1 | 5/2015 | Schurman et al. |
| 2015/0133755 | A1 | 5/2015 | Smith et al. |
| 2015/0140863 | A1 | 5/2015 | Al-Ali et al. |
| 2015/0141781 | A1 | 5/2015 | Weber et al. |
| 2015/0165312 | A1 | 6/2015 | Kiani |
| 2015/0196237 | A1 | 7/2015 | Lamego |
| 2015/0196249 | A1 | 7/2015 | Brown et al. |
| 2015/0201874 | A1 | 7/2015 | Diab |
| 2015/0208966 | A1 | 7/2015 | Ai-Ali |
| 2015/0216459 | A1 | 8/2015 | Al-Ali et al. |
| 2015/0230755 | A1 | 8/2015 | Al-Ali et al. |
| 2015/0238722 | A1 | 8/2015 | Al-Ali |
| 2015/0245773 | A1 | 9/2015 | Lamego et al. |
| 2015/0245794 | A1 | 9/2015 | Al-Ali |
| 2015/0257689 | A1 | 9/2015 | Al-Ali et al. |
| 2015/0272514 | A1 | 10/2015 | Kiani et al. |
| 2015/0351697 | A1 | 12/2015 | Weber et al. |

(56) References Cited

U.S. PATENT DOCUMENTS

| | | | |
|---|---|---|---|
| 2015/0351704 | A1 | 12/2015 | Kiani et al. |
| 2015/0359429 | A1 | 12/2015 | Al-Ali et al. |
| 2015/0366472 | A1 | 12/2015 | Kiani |
| 2015/0366507 | A1 | 12/2015 | Blank |
| 2015/0374298 | A1 | 12/2015 | Al-Ali et al. |
| 2015/0380875 | A1 | 12/2015 | Coverston et al. |
| 2016/0000362 | A1 | 1/2016 | Diab et al. |
| 2016/0007930 | A1 | 1/2016 | Weber et al. |
| 2016/0029932 | A1 | 2/2016 | Al-Ali |
| 2016/0029933 | A1 | 2/2016 | Al-Ali et al. |
| 2016/0045118 | A1 | 2/2016 | Kiani |
| 2016/0051205 | A1 | 2/2016 | Al-Ali et al. |
| 2016/0058338 | A1 | 3/2016 | Schurman et al. |
| 2016/0058347 | A1 | 3/2016 | Reichgott et al. |
| 2016/0066823 | A1 | 3/2016 | Kind et al. |
| 2016/0066824 | A1 | 3/2016 | Al-Ali et al. |
| 2016/0072429 | A1 | 3/2016 | Kiani et al. |
| 2016/0073967 | A1 | 3/2016 | Lamego et al. |
| 2016/0081552 | A1 | 3/2016 | Wojtczuk et al. |
| 2016/0095543 | A1 | 4/2016 | Telfort et al. |
| 2016/0095548 | A1 | 4/2016 | Al-Ali et al. |
| 2016/0103598 | A1 | 4/2016 | Al-Ali et al. |
| 2016/0113527 | A1 | 4/2016 | Al-Ali et al. |
| 2016/0143548 | A1 | 5/2016 | Al-Ali |
| 2016/0166182 | A1 | 6/2016 | Al-Ali et al. |
| 2016/0166183 | A1 | 6/2016 | Poeze et al. |
| 2016/0166188 | A1 | 6/2016 | Bruinsma et al. |
| 2016/0166210 | A1 | 6/2016 | Ai-Ali |
| 2016/0192869 | A1 | 7/2016 | Kiani et al. |
| 2016/0196388 | A1 | 7/2016 | Lam ego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0000394 | A1 | 1/2017 | Al-Ali et al. |
| 2017/0007134 | A1 | 1/2017 | Al-Ali et al. |
| 2017/0014083 | A1 | 1/2017 | Diab et al. |
| 2017/0014084 | A1 | 1/2017 | Al-Ali et al. |
| 2017/0024748 | A1 | 1/2017 | Haider |
| 2017/0027456 | A1 | 2/2017 | Kinast et al. |
| 2017/0042488 | A1 | 2/2017 | Muhsin |
| 2017/0055847 | A1 | 3/2017 | Kiani et al. |
| 2017/0055851 | A1 | 3/2017 | Al-Ali |
| 2017/0055882 | A1 | 3/2017 | Al-Ali et al. |
| 2017/0055887 | A1 | 3/2017 | Al-Ali |
| 2017/0055896 | A1 | 3/2017 | Al-Ali et al. |
| 2017/0086723 | A1 | 3/2017 | Al-Ali et al. |
| 2017/0143281 | A1 | 5/2017 | Olsen |
| 2017/0147774 | A1 | 5/2017 | Kiani |
| 2017/0156620 | A1 | 6/2017 | Al-Ali et al. |
| 2017/0173632 | A1 | 6/2017 | Al-Ali |
| 2017/0187146 | A1 | 6/2017 | Kiani et al. |
| 2017/0188919 | A1 | 7/2017 | Al-Ali et al. |
| 2017/0196464 | A1 | 7/2017 | Jansen et al. |
| 2017/0196470 | A1 | 7/2017 | Lamego et al. |
| 2017/0202490 | A1 | 7/2017 | Al-Ali et al. |
| 2017/0224231 | A1 | 8/2017 | Al-Ali |
| 2017/0224262 | A1 | 8/2017 | Ai-Ali |
| 2017/0228516 | A1 | 8/2017 | Sampath et al. |
| 2017/0245790 | A1 | 8/2017 | Al-Ali et al. |
| 2017/0251974 | A1 | 9/2017 | Shreim et al. |
| 2017/0251975 | A1 | 9/2017 | Shreim et al. |
| 2017/0258403 | A1 | 9/2017 | Abdul-Hafiz et al. |
| 2017/0311891 | A1 | 11/2017 | Kiani et al. |
| 2017/0325728 | A1 | 11/2017 | Al-Ali et al. |
| 2017/0332976 | A1 | 11/2017 | Al-Ali et al. |
| 2017/0340293 | A1 | 11/2017 | Al-Ali et al. |
| 2017/0360310 | A1 | 12/2017 | Kiani et al. |
| 2017/0367632 | A1 | 12/2017 | Al-Ali et al. |
| 2018/0008146 | A1 | 1/2018 | Al-Ali et al. |
| 2018/0014752 | A1 | 1/2018 | Al-Ali et al. |
| 2018/0028124 | A1 | 2/2018 | Al-Ali et al. |
| 2018/0055385 | A1 | 3/2018 | Al-Ali |
| 2018/0055390 | A1 | 3/2018 | Kiani et al. |
| 2018/0055430 | A1 | 3/2018 | Diab et al. |
| 2018/0064381 | A1 | 3/2018 | Shakespeare et al. |
| 2018/0069776 | A1 | 3/2018 | Lamego et al. |
| 2018/0103874 | A1 | 4/2018 | Lee et al. |
| 2018/0116575 | A1 | 5/2018 | Perea et al. |
| 2018/0125368 | A1 | 5/2018 | Lamego et al. |
| 2018/0125430 | A1 | 5/2018 | Al-Ali et al. |
| 2018/0125445 | A1 | 5/2018 | Telfort et al. |
| 2018/0130325 | A1 | 5/2018 | Kiani et al. |
| 2018/0132769 | A1 | 5/2018 | Weber et al. |
| 2018/0132770 | A1 | 5/2018 | Lamego |
| 2018/0153446 | A1 | 6/2018 | Kiani |
| 2018/0206815 | A1 | 7/2018 | Telfort |
| 2018/0242926 | A1 | 8/2018 | Muhsin et al. |
| 2018/0247353 | A1 | 8/2018 | Al-Ali et al. |
| 2018/0247712 | A1 | 8/2018 | Muhsin et al. |
| 2018/0256087 | A1 | 9/2018 | Al-Ali et al. |
| 2018/0296161 | A1 | 10/2018 | Shreim et al. |
| 2018/0300919 | A1 | 10/2018 | Muhsin et al. |
| 2018/0310822 | A1 | 11/2018 | Indorf et al. |
| 2018/0310823 | A1 | 11/2018 | Al-Ali et al. |
| 2018/0317826 | A1 | 11/2018 | Muhsin et al. |
| 2019/0015023 | A1 | 1/2019 | Monfre |
| 2019/0117070 | A1 | 4/2019 | Muhsin et al. |
| 2019/0142344 | A1 | 5/2019 | Telfort et al. |
| 2019/0200941 | A1 | 7/2019 | Chandran et al. |
| 2019/0239787 | A1 | 8/2019 | Pauley et al. |
| 2019/0320906 | A1 | 10/2019 | Olsen |
| 2019/0374139 | A1 | 12/2019 | Kiani et al. |
| 2019/0374173 | A1 | 12/2019 | Kiani et al. |
| 2019/0374713 | A1 | 12/2019 | Kiani et al. |
| 2020/0060869 | A1 | 2/2020 | Telfort et al. |
| 2020/0111552 | A1 | 4/2020 | Ahmed |
| 2020/0113435 | A1 | 4/2020 | Muhsin |
| 2020/0113488 | A1 | 4/2020 | Al-Ali et al. |
| 2020/0113496 | A1 | 4/2020 | Scruggs et al. |
| 2020/0113497 | A1 | 4/2020 | Triman et al. |
| 2020/0113520 | A1 | 4/2020 | Abdul-Hafiz et al. |
| 2020/0138288 | A1 | 5/2020 | Al-Ali et al. |
| 2020/0138368 | A1 | 5/2020 | Kiani et al. |
| 2020/0163597 | A1 | 5/2020 | Dalvi et al. |
| 2020/0196877 | A1 | 6/2020 | Vo et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0321793 | A1 | 10/2020 | Al-Ali et al. |
| 2020/0329983 | A1 | 10/2020 | Al-Ali et al. |
| 2020/0329984 | A1 | 10/2020 | Al-Ali et al. |
| 2020/0329993 | A1 | 10/2020 | Al-Ali et al. |
| 2020/0330037 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0113121 | A1 | 4/2021 | Diab et al. |
| 2021/0117525 | A1 | 4/2021 | Kiani et al. |
| 2021/0118581 | A1 | 4/2021 | Kiani et al. |
| 2021/0121582 | A1 | 4/2021 | Krishnamani et al. |
| 2021/0161465 | A1 | 6/2021 | Barker et al. |
| 2021/0236729 | A1 | 8/2021 | Kiani et al. |
| 2021/0256835 | A1 | 8/2021 | Ranasinghe et al. |
| 2021/0275101 | A1 | 9/2021 | Vo et al. |
| 2021/0290060 | A1 | 9/2021 | Ahmed |
| 2021/0290072 | A1 | 9/2021 | Forrest |
| 2021/0290080 | A1 | 9/2021 | Ahmed |
| 2021/0290120 | A1 | 9/2021 | Al-Ali |
| 2021/0290177 | A1 | 9/2021 | Novak, Jr. |

(56) References Cited

U.S. PATENT DOCUMENTS

| | | | |
|---|---|---|---|
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0039707 | A1 | 2/2022 | Sharma et al. |
| 2022/0053892 | A1 | 2/2022 | Al-Ali et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Ai-Ali |
| 2023/0038389 | A1 | 2/2023 | Vo |
| 2023/0045647 | A1 | 2/2023 | Vo |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Ai-Ali |
| 2024/0188872 | A1 | 6/2024 | Al-Ali et al. |
| 2024/0245855 | A1 | 7/2024 | Vo et al. |
| 2024/0260894 | A1 | 8/2024 | Olsen |
| 2024/0267698 | A1 | 8/2024 | Telfort et al. |
| 2024/0277233 | A1 | 8/2024 | Ai-Ali |
| 2024/0277280 | A1 | 8/2024 | Ai-Ali |
| 2024/0298920 | A1 | 9/2024 | Fernkbist et al. |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |
| 2025/0255764 | A1 | 8/2025 | Stead |
| 2025/0278512 | A1 | 9/2025 | Koo et al. |
| 2025/0281059 | A1 | 9/2025 | Avendano |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |
| 2025/0318761 | A1 | 10/2025 | Al-Ali et al. |
| 2025/0322950 | A1 | 10/2025 | Al-Ali et al. |
| 2025/0323417 | A1 | 10/2025 | Rey |
| 2025/0329240 | A1 | 10/2025 | Kiani |
| 2025/0344010 | A1 | 11/2025 | Al-Ali et al. |
| 2026/0014333 | A1 | 1/2026 | Fernkvist et al. |
| 2026/0014334 | A1 | 1/2026 | Danwihl |
| 2026/0048198 | A1 | 2/2026 | Vo et al. |

FOREIGN PATENT DOCUMENTS

| | | | | |
|---|---|---|---|---|
| CN | 201497610 | | 6/2010 | |
| CN | 202005761 | | 10/2011 | |
| EP | 0716628 | | 12/1998 | |
| EP | 0659058 | | 1/1999 | |
| EP | 0 956 820 | | 11/1999 | |
| EP | 1518442 | | 3/2005 | |
| EP | 2 014 234 | | 1/2009 | |
| EP | 1207536 | | 2/2010 | |
| EP | 2488106 | | 8/2012 | |
| EP | 2488978 | | 8/2012 | |
| FR | 2 847 796 | | 6/2004 | |
| GB | 2358546 | | 7/2001 | |
| JP | S56-031742 | A | 3/1961 | |
| JP | S53-094482 | | 8/1978 | |
| JP | 60059900 | | 4/1985 | |
| JP | 6214898 | | 1/1987 | |
| JP | 01-309872 | | 12/1989 | |
| JP | H04-317637 | A | 11/1992 | |
| JP | H07-152553 | | 6/1995 | |
| JP | 10-155755 | | 6/1998 | |
| JP | 2001-50713 | | 2/2001 | |
| JP | 2003-329719 | | 11/2003 | |
| JP | 2005-522292 | | 7/2005 | |
| JP | 2005-531230 | A | 10/2005 | |
| JP | 2012-513872 | | 6/2012 | |
| JP | 2013-508029 | | 3/2013 | |
| JP | 2013-508030 | | 3/2013 | |
| NO | 20040819 | | 2/2004 | |
| WO | WO 1994/005207 | | 3/1994 | |
| WO | WO 1994/013207 | | 6/1994 | |
| WO | WO 1995/029632 | | 11/1995 | |
| WO | WO 1999/053277 | | 10/1999 | |
| WO | WO-9953277 | A1 * | 10/1999 | ............... A61B 7/04 |
| WO | WO 2000/010462 | | 3/2000 | |
| WO | WO 2001/034033 | | 5/2001 | |
| WO | WO 01/087005 | | 11/2001 | |
| WO | WO 2001/097691 | | 12/2001 | |
| WO | WO 2001/078059 | | 3/2002 | |
| WO | WO 02/024067 | | 7/2002 | |
| WO | WO 2002/003042 | | 12/2002 | |
| WO | WO 2003/058646 | | 7/2003 | |
| WO | WO 2003/087737 | | 10/2003 | |
| WO | WO 2004/000111 | | 12/2003 | |
| WO | WO 2004/004411 | | 1/2004 | |
| WO | WO 2004/078038 | | 9/2004 | |
| WO | WO 2005/096931 | | 10/2005 | |
| WO | WO 2005/099562 | | 10/2005 | |
| WO | WO 2008/017246 | | 2/2008 | |
| WO | WO 2008/148172 | | 12/2008 | |
| WO | WO 2009/137524 | | 11/2009 | |
| WO | WO 2009/155593 | | 12/2009 | |
| WO | WO 2010/078168 | | 7/2010 | |
| WO | WO 2011/047211 | | 4/2011 | |
| WO | WO 2011/047213 | | 4/2011 | |
| WO | WO 2011/047216 | | 8/2011 | |
| WO | WO 2011/047207 | | 9/2011 | |
| WO | WO 2011/047209 | | 3/2012 | |
| WO | WO 2013/056141 | | 4/2013 | |

OTHER PUBLICATIONS

US 8,845,543 B2, 09/2014, Diab et al. (withdrawn)
US 2024/0016391 A1, 01/2024, Lapotko et al. (withdrawn)
Analog Devices, 12-Bit Serial Input Multiplying D/A Converter, Product Data Sheet, 2000.
Avago Technologies, "HCNR200 and HCNR201, High-Linearity Analog Optocouplers," Data Sheet, Avago Technologies, Nov. 18, 2008.

(56) References Cited

OTHER PUBLICATIONS

Eldor et al., "A device for monitoring ventilation during anesthesia; the paratracheal audible respiratory monitor", Canadian Journal of Anesthesia, 1990, vol. 9, No. 1, p. 95-98.
Images showing tear down of a Measurement Specialties' stethoscope, Images taken on Sep. 7, 2007, in 38 pages.
Sierra et al., Monitoring Respiratory Rate Based on Tracheal Sounds. First Experiences, Proceedings of the 26th Annual Int'l Conf. of the IEEE EMBS (Sep. 2004), 317-320.
WelchAllyn OEM Technologies, ECG ASIC, ECG 3-lead, 5-lead, 12-lead and RESP Signal Processing, ECG ASIC Part No. 000.91163 (2001).
White, "Advanced Compression Techniques, Tips & Tricks", Part 1 and Part 2, Dec. 2000 and Jan. 2001 in 11 pages.
Oversampling by Wikipedia, the free encyclopedia, pub. Online Oct. 7, 2012 at "https://wikipedia.org/w/index.php?title=Oversampling&oldid=516454012", accessed Sep. 3, 2015.
Pseudorandom noise by Wikipedia, the free encyclopedia, pub. Online Jul. 25, 2012 at "https://wikipedia.org/w/index.php?title=Pseudorandom_noise&oldid=504121479", accessed Sep. 3, 2015.
Noise generator by Wikipedia, the free encyclopedia, pub. Online May 6, 2012 at "https://wikipedia.org/w/index.php?title=Noise_generator&oldid=490897729", accessed Sep. 3, 2015.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report and Written Opinion for PCT/US2009/042902, mailed Dec. 8, 2009.
International Search Report and Written Opinion in PCT/US2009/042902 mailed Aug. 12, 2009 in 16 pages.
International Search Report, PCT Application PCT/CA2003/000536, Dec. 11, 2003; 2 pages.
EP Office Action dated May 18, 2011 in application No. 03711767.8.
Japanese Office Action re Application No. 2007-506626, dated Mar. 1, 2011.
PCT Invitation to Pay Fees and Initial Search Report in PCT/US2010/052756, dated Oct. 5, 2011.
International Search Report and Written Opinion in PCT/US2010/052756 mailed Feb. 6, 2012 in 15 pages.
International Search Report & Written Opinion for PCT/US2010/052756, mailed Feb. 6, 2012; 17 pages.
EP Office Action dated Oct. 16, 2018 in application No. 10773191.1.
PCT Invitation to Pay Fees and Initial Search Report in PCT/US2009/069287, dated Apr. 21, 2010.
International Search Report and Written Opinion issued in PCT Application No. PCT/US2009/069287, Jun. 30, 2010.
Office Action in Japanese Application No. 2011-544508 mailed Apr. 30, 2014.
EP Office Action dated Mar. 5, 2013 in application No. 10779086.7.
EP Office Action dated Jul. 11, 2016 in application No. 10779086.7.
EP Office Action dated May 12, 2017 in application No. 10779086.7.
EP Office Action dated Dec. 10, 2018 in application No. 10779086.7.
PCT Invitation to Pay Fees and Initial Search Report in PCT/US2010/052754, dated Mar. 15, 2011.
International Search Report and Written Opinion in PCT/US2010/052754 mailed Jul. 27, 2011.
International Preliminary Report on Patentability (IPRP) in PCT/US2010/052754 dated Apr. 26, 2012 in 11 pages.
International Search Report and Written Opinion in PCTUS2010052760 mailed Mar. 8, 2011 in 11 pages.
International Search Report and Written Opinion in PCT/US2010/052760 mailed Mar. 8, 2011 in 9 pages.
International Search Report and Written Opinion in PCT/US2010/052763, mailed May 13, 2011.
International Preliminary Report on Patentability in PCT/US2010/052763 dated Apr. 17, 2012 in 9 pages.
International Search Report and Written Opinion in PCT Application No. PCT/US2012/060084 dated Dec. 21, 2012 in 11 pages.
International Preliminary Report on Patentability dated Apr. 15, 2014 for PCT Application No. PCT/US2012/060084.
Office Action in European Application No. 12784142.7 dated Apr. 10, 2018 in 5 pages.
European Search Report for Application No. 13185148.7 dated Dec. 6, 2013.
Office Action for Application No. 13185148.7 dated Apr. 4, 2017.
Office Action for Application No. 13185148.7 dated Nov. 7, 2017.
Office Action for Application No. 13185148.7 dated Jun. 7, 2018.
Office Action for Application No. 13185148.7 dated Apr. 4, 2019.
GE Healthcare, "Transport Pro™ Patient Monitor" Operator's Manual, Software Version 2.1, Apr. 9, 2007, 286 pages.
Office Action in European Application No. 19182152.9 dated Nov. 4, 2019 in 10 pages.
Office Action in European Application No. 20175965.1 dated Oct. 12, 2020 in 7 pages.

* cited by examiner

ACOUSTIC RESPIRATORY MONITORING SYSTEMS AND METHODS

CROSS-REFERENCE TO RELATED APPLICATIONS

This present application is a continuation of U.S. patent application Ser. No. 12/904,789, entitled "Acoustic Respiratory Monitoring Systems And Methods," filed Oct. 14, 2010, which claims priority benefit to U.S. Provisional Application No. 61/252,099, filed Oct. 15, 2009, each of which is hereby incorporated by reference in its entirety.

Additionally, this application relates to the following U.S. patent applications, each of which is incorporated by reference in its entirety:

| application No. | Filing Date | Title | Attorney Docket |
|---|---|---|---|
| 60/893853 | Mar. 8, 2007 | MULTI-PARAMETER PHYSIOLOGICAL MONITOR | MCAN.014PR |
| 60/893850 | Mar. 8, 2007 | BACKWARD COMPATIBLE PHYSIOLOGICAL SENSOR WITH INFORMATION ELEMENT | MCAN.015PR |
| 60/893858 | Mar. 8, 2007 | MULTI-PARAMETER SENSOR FOR PHYSIOLOGICAL MONITORING | MCAN.016PR |
| 60/893856 | Mar. 8, 2007 | PHYSIOLOGICAL MONITOR WITH FAST GAIN ADJUST DATA ACQUISITION | MCAN.017PR |
| 12/044883 | Mar. 8, 2008 | SYSTEMS AND METHODS FOR DETERMINING A PHYSIOLOGICAL CONDITION USING AN ACOUSTIC MONITOR | MCAN.014A |
| 61/252083 | Oct. 15, 2009 | DISPLAYING PHYSIOLOGICAL INFORMATION | MCAN.019PR |
| 12/904836 | Oct. 14, 2010 | BIDIRECTIONAL PHYSIOLOGICAL INFORMATION DISPLAY | MCAN.019A1 |
| 12/904823 | Oct. 14, 2010 | BIDIRECTIONAL PHYSIOLOGICAL INFORMATION DISPLAY | MCAN.019A2 |
| 61/141584 | Dec. 30, 2008 | ACOUSTIC SENSOR ASSEMBLY | MCAN.030PR |
| 61/252076 | Oct. 15, 2009 | ACOUSTIC SENSOR ASSEMBLY | MCAN.030PR2 |
| 12/643939 | Dec. 21, 2009 | ACOUSTIC SENSOR ASSEMBLY | MCAN.030A |
| 61/313645 | Mar. 12, 2010 | ACOUSTIC RESPIRATORY MONITORING SENSOR HAVING MULTIPLE SENSING ELEMENTS | MCAN.033PR2 |
| 12/904931 | Oct. 14, 2010 | ACOUSTIC RESPIRATORY MONITORING SENSOR HAVING MULTIPLE SENSING ELEMENTS | MCAN.033A |
| 12/904890 | Oct. 14, 2010 | ACOUSTIC RESPIRATORY MONITORING SENSOR HAVING MULTIPLE SENSING ELEMENTS | MCAN.033A2 |
| 12/904938 | Oct. 14, 2010 | ACOUSTIC RESPIRATORY MONITORING SENSOR HAVING MULTIPLE SENSING ELEMENTS | MCAN.033A3 |
| 12/904907 | Oct. 14, 2010 | ACOUSTIC PATIENT SENSOR | MCAN.033A4 |
| 61/252062 | Oct. 15, 2010 | PULSE OXIMETRY SYSTEM WITH LOW NOISE CABLE HUB | MCAN.035PR |
| 61/265730 | Dec. 1, 2009 | PULSE OXIMETRY SYSTEM WITH ACOUSTIC SENSOR | MCAN.035PR3 |
| 12/904775 | Oct. 14, 2010 | PULSE OXIMETRY SYSTEM WITH LOW NOISE CABLE HUB | MCAN.035A |
| 12/905036 | Oct. 14, 2010 | PHYSIOLOGICAL ACOUSTIC MONITORING SYSTEM | MCAN.046A |
| 61/331087 | May 4, 2010 | ACOUSTIC RESPIRATION DISPLAY | MASIM0.800PR2 |
| 61/391098 | Oct. 8, 2010 | ACOUSTIC MONITOR | MCAN-P001 |

Many of the embodiments described herein are compatible with embodiments described in the above related applications. Moreover, some or all of the features described herein can be used or otherwise combined with many of the features described in the applications listed above.

BACKGROUND

Field

The present disclosure relates to non-invasive biological parameter sensing, including sensing using acoustic sensors and related systems and methods.

Description of the Related Art

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for reliable acoustic respiratory monitoring systems.

SUMMARY

There are often a wide variety of types and intensities of sounds present in a physiological monitoring environment. Thus, it is often desirable to accurately process a wide range of physiological sounds. For example, in many circumstances, medical personnel would benefit from the ability to monitor, record and/or reproduce physiological sounds ranging from relatively low intensity to relatively high intensity physiological sounds.

According to certain aspects described herein, an acoustic sensor is configured to accurately capture a wide range of physiological sound content. Such sounds can include a relatively wide range of physiological sounds, including relatively quiet sounds such as breath, soft speech, heart sounds, etc., as well as relatively loud sounds such as loud speech, coughing, gasping, and the like.

To achieve these and other benefits, componentry in the sensor data path generally compresses, reduces, or otherwise modifies a signal output by a sensing element or other component, improving the overall dynamic range of the sensor. For example, a piezoelectric film or other sensing element may have a relatively high input dynamic range, and may therefore be capable of generating a signal representing a wide range of sound intensity values. The sensing element may also have a relatively high output dynamic range and thus have a large range of possible output signal values (e.g., voltage values). However, one or more subsequent components in the sensor data path, such as a preamplifier or other circuit, may have a relatively lower input dynamic range, and thus be capable of processing a range of input signal values that is significantly smaller than the range of values produced by the sensing element.

If the unmodified signal from the sensing element is provided to the preamplifier, the preamplifier may saturate or otherwise produce a distorted output for signal values received by the sensing element that are above a threshold value (e.g., saturation threshold). This can result in a loss of sound content, and a corresponding reduction in the overall dynamic range of the sensor. To mitigate such losses, certain techniques described herein compress or otherwise modify the signal produced by the sensing element, and provide the compressed signal to the preamplifier or other subsequent sensor stage. The signal is compressed sufficiently to prevent saturation at the preamplifier for a desired range of signal values, thereby improving the overall dynamic range of the sensor. For example, the signal may be compressed based on the input dynamic range of the preamplifier or other relatively low dynamic range component. In additional embodiments, the output of the lower dynamic range component (e.g., preamplifier or other component) is compressed directly instead of, or in addition to, compressing the sensing element output.

Additionally, while compression can have distortive effects on the sound signal, such distortions can be advantageously removed or reduced according to certain aspects by performing a decompression operation. Such an operation can be performed before providing the signal for output for display, for the processing of physiological characteristics, and the like.

As will be described, acoustic sensors and systems provided herein, such as those having the above-described capabilities and/or other capabilities described herein, can be suited for a variety of beneficial applications, including enhanced physiological monitoring, sound processing, audio communication, identification and handling of medical emergencies, and the like.

An acoustic sensor is provided according to certain aspects for non-invasively detecting physiological acoustic vibrations indicative of one or more physiological parameters of a medical patient. The sensor can include an acoustic sensing element configured to generate a first signal in response to acoustic vibrations from a medical patient. The sensor can also include front-end circuitry configured to receive an input signal that is based at least in part on the first signal and to produce an amplified signal in response to the input signal. In some embodiments, the sensor further includes a compression module in communication with the front-end circuitry and configured to compress portions of at least one of the input signal and the amplified signal according to a first compression scheme, the compressed portions corresponding to portions of the first signal having a magnitude greater than a predetermined threshold level.

In certain embodiments, an acoustic sensor is provided for non-invasively detecting physiological acoustic vibrations indicative of one or more physiological parameters of a medical patient. The acoustic sensor can include a sensing element configured to generate an output signal in response to acoustic vibrations from a medical patient. The acoustic sensing element according to certain embodiments has an output dynamic range. The front-end circuitry can be in communication with the acoustic sensing element and have a dynamic range. In some embodiments, the dynamic range of the front-end circuitry is less than the output dynamic range of the acoustic sensing element. The sensor can further include a dynamic range module configured, in response to the output signal, to maintain the output signal's intensity within the dynamic range of the front-end circuitry.

In certain embodiments, a method is provided for increasing the dynamic range of a sensor capable of non-invasively detecting physiological acoustic vibrations indicative of one or more physiological parameters of a medical patient, comprising. The method can include outputting a first signal using a first sensing element and in response to acoustic vibrations from a medical patient. The method can also include generating an amplified signal using front-end circuitry and in response an input signal that is based at least in part on the first signal. In certain embodiments, the method also includes compressing portions of at least one of the input signal and the amplified signal according to a first compression scheme. The compressed portions may correspond to portions of the first signal having a magnitude greater than a predetermined threshold level, for example.

In certain embodiments, a method of improving the dynamic range of an acoustic respiratory monitoring system is provided. The method includes providing an acoustic sensor comprising a sensing element configured to detect acoustic vibrations at a measurement site of a medical patient. The method further includes receiving a signal indicative of acoustic vibrations from the acoustic sensor. The method also includes compressing the signal to avoid saturation when the signal amplitude exceeds a predetermined threshold.

An acoustic respiratory monitor is provided including an acoustic sensor input configured to receive a signal indicative of acoustic vibrations from an acoustic sensor attached to a measurement site of a medical patient. The respiratory monitor also includes a compression module configured to compress the signal to avoid saturation when the signal amplitude exceeds a predetermined threshold.

A method of non-invasively sensing one or more physiological parameters of a medical patient is provided. The method includes providing a plurality of acoustic sensors each comprising a sensing element configured to detect acoustic vibrations, each of the plurality of acoustic sensors configured to attach to a corresponding measurement site on a medical patient. The method further includes receiving a plurality of signals indicative of acoustic vibrations detected by the plurality of acoustic sensors, each of the plurality of signals comprising a physiological signal component and a noise component. The method of certain embodiments also includes processing the plurality of signals to generate a reduced noise signal indicative of a physiological parameter of the medical patient. The method of claim 1, wherein the reduced noise signal has a higher signal-to-noise ratio than any of the plurality of signals. The processing can comprise performing a cross-correlation using the plurality of signals. The processing can performing a shift-and-add operation using the plurality of signals. The processing in some embodiments comprises locating a point of maximum energy between two of the signals. The processing in yet additional embodiments comprises shifting one or more of the plurality of signals with respect to one or more of the other signals so that the physiological components of the signals are substantially in phase with respect to one another. The processing can include combining the plurality of signals together after the shifting. The noise components of the plurality of signals are substantially out of phase with respect to one another after the shifting in some embodiments.

A system for non-invasively sensing one or more physiological parameters of a medical patient is provided. The system includes a plurality of acoustic sensors each comprising a sensing element configured to detect acoustic vibrations. The plurality of acoustic sensors are configured to be attached to a corresponding plurality of measurement sites on a medical patient. The system further includes a processor configured to receive a signal from each of said acoustic sensors, each signal having a physiological signal component and a noise component. Each signal is further indicative of acoustic vibrations detected by the plurality of acoustic sensors. The processor is also configured to process the signals to generate a reduced noise signal indicative of a physiological parameter of the medical patient. In some embodiments, the reduced noise signal has a higher signal-to-noise ratio than any of the plurality of signals. In some embodiments, processor is further configured to perform a cross-correlation using the plurality of signals. In some embodiments, the processor is further configured to perform a shift-and-add operation using the plurality of signals. In embodiments, the processor is further configured to determine a point of maximum energy between two of the signals. The processor can be configured to: shift one or more of the plurality of signals with respect to one or more of the other signals such that the physiological components of the signals are substantially in phase with respect to one another; and combine the plurality of signals together after the shifting. Moreover, the noise components of the plurality of signals are substantially out of phase with respect to one another after the shifting in some embodiments. In some embodiments, the plurality of acoustic sensors are connected together via at least one monitor cable.

In certain embodiments, a method of determining a tissue characterization parameter of tissue at a measurement site using an active acoustic sensor of an acoustic respiratory monitoring system is provided. The method includes providing an acoustic sensor comprising a sensing element configured to transmit and detect acoustic vibrations. The method further includes transmitting first acoustic vibrations into a measurement site of a medical patient with the sensor. The method also includes detecting second acoustic vibrations with the acoustic sensor, the detected second acoustic vibrations being generated at least in part in response to the transmitted first acoustic vibration. In certain embodiments, the method also includes processing a signal indicative of the detected second acoustic vibrations to determine a tissue characterization parameter. In certain embodiments, the tissue characterization parameter indicates integrity of a mechanical connection between the acoustic sensor and the measurement site. In some embodiments, the tissue characterization parameter is a probe-off condition. In yet other embodiments, the tissue characterization parameter indicates a tissue type. In some embodiments, the tissue characterization parameter indicates a tissue composition. The processing can further comprise removing noise from the signal based on the detected second acoustic vibrations.

An acoustic respiratory monitor configured to determine a tissue characterization parameter at a tissue measurement site using an active acoustic sensor, the acoustic respiratory monitor is provided in certain embodiments. The monitor includes an active acoustic sensor port configured for attachment with an active acoustic sensor coupled to a measurement site of a medical patient. In certain embodiments, the active acoustic sensor has a sensing element configured to transmit and detect acoustic vibrations. The monitor further includes a processor configured to transmit a first signal to the active sensor port, the transmitted first signal configured to cause the active acoustic sensor to transmit a first acoustic vibration to the measurement site. The processor is also configured to receive a second signal from the active sensor port, the received second signal indicative of acoustic vibrations detected by the active acoustic sensor. The process may also be configured to process the received second signal indicative of the detected acoustic vibrations to determine a tissue characterization parameter. In certain embodiments, the sensing element comprises a single piezoelectric membrane. The sensing element can comprise a first piezoelectric membrane configured to transmit acoustic vibrations and a second piezoelectric member configured to detect acoustic vibrations. In some embodiments, tissue characterization parameter indicates integrity of a mechanical connection between the acoustic sensor and the measurement site.

A method of generating an auscultatory output with an acoustic respiratory monitor is provided in certain embodiments. The method comprises providing an acoustic respiratory monitor configured to receive a signal indicative of a physiological parameter of a medical patient from an acoustic sensor attached to the medical patient. The method also includes generating an output signal corresponding to the physiological parameter, the output signal being audible to a clinician when provided to an acoustic transducer. The method also includes providing the output signal to the clinician via a communication link. The acoustic sensor can include piezoelectric membrane. In some embodiments, the communication link comprises a wireless communication link. The providing can comprises providing the output signal to the connection over the Internet, for example.

An acoustic respiratory monitor configured to provide an auscultatory output to remote location is provided in certain embodiments. The monitor includes an acoustic sensor input configured to receive a signal indicative of a physiological parameter of a medical patient from an acoustic sensor attached to the medical patient. The monitor also includes a processor configured to generate an output signal corresponding to the physiological parameter, the output signal being audible to a clinician when provided to an acoustic transducer. The method further includes a communication module, configured to communicate the output signal to the clinician via a communication link. In certain embodiments, the acoustic sensor comprises a piezoelectric membrane. The communication module can comprise a wireless transmitter. The communication module can also be configured to communicate to the clinician over the Internet.

DETAILED DESCRIPTION

Various embodiments will be described hereinafter with reference to the accompanying drawings. These embodiments are illustrated and described by example only, and are not intended to be limiting.

System Overview

In various embodiments, an acoustic sensor configured to operate with a physiological monitoring system includes an acoustic signal processing system that measures and/or determines any of a variety of physiological parameters of a medical patient. For example, in one embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate which can be used to determine a probe off condition, heart sounds (S1, S2, S3, S4, and murmurs, etc.), and change in heart sounds such as normal to murmur or split heart sounds indicating fluid overload.

Moreover, the acoustic signal processing system may: (1) use one or more additional probes to detect additional heart sounds; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 4A:
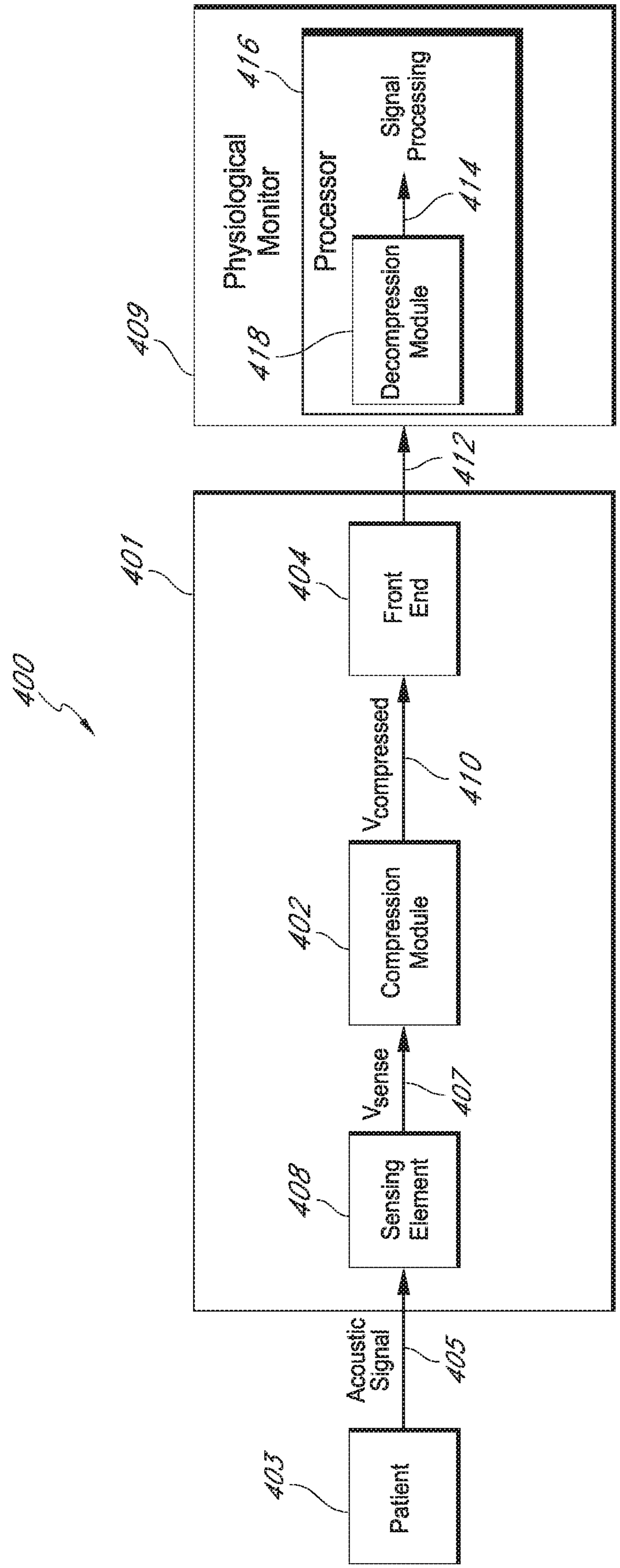
FIG. 4A is a schematic diagram of one embodiment of a system including a sensor configured to perform dynamic range compression.
Figure 4B:
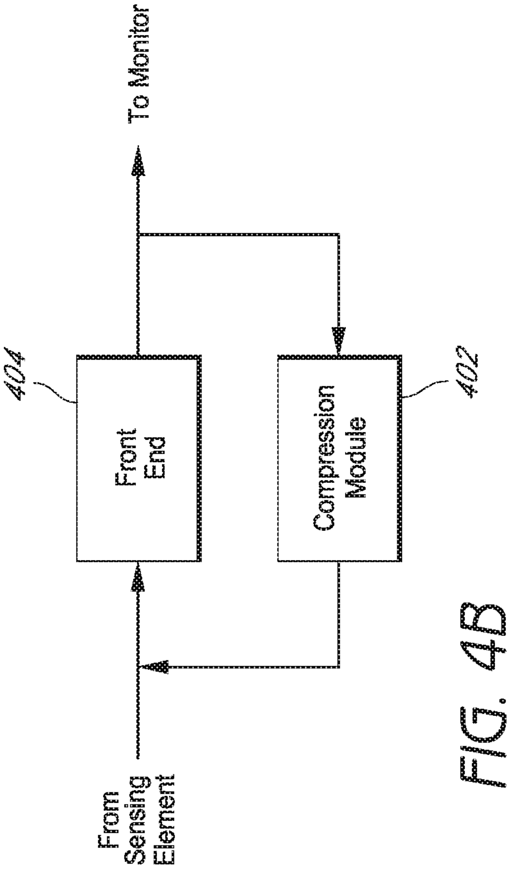
FIGS. 4B and 4C are schematic diagrams illustrating additional dynamic range compression architectures according to certain embodiments.
Figure 4C:
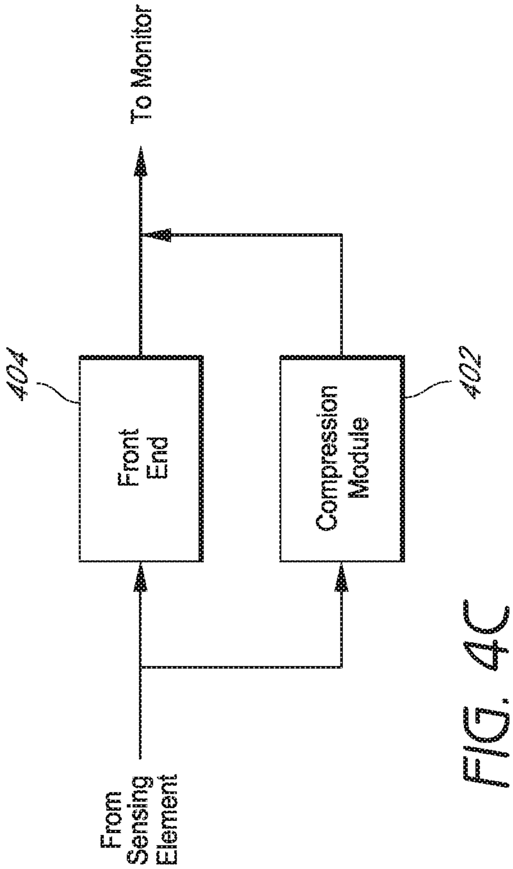
Figure 4D:
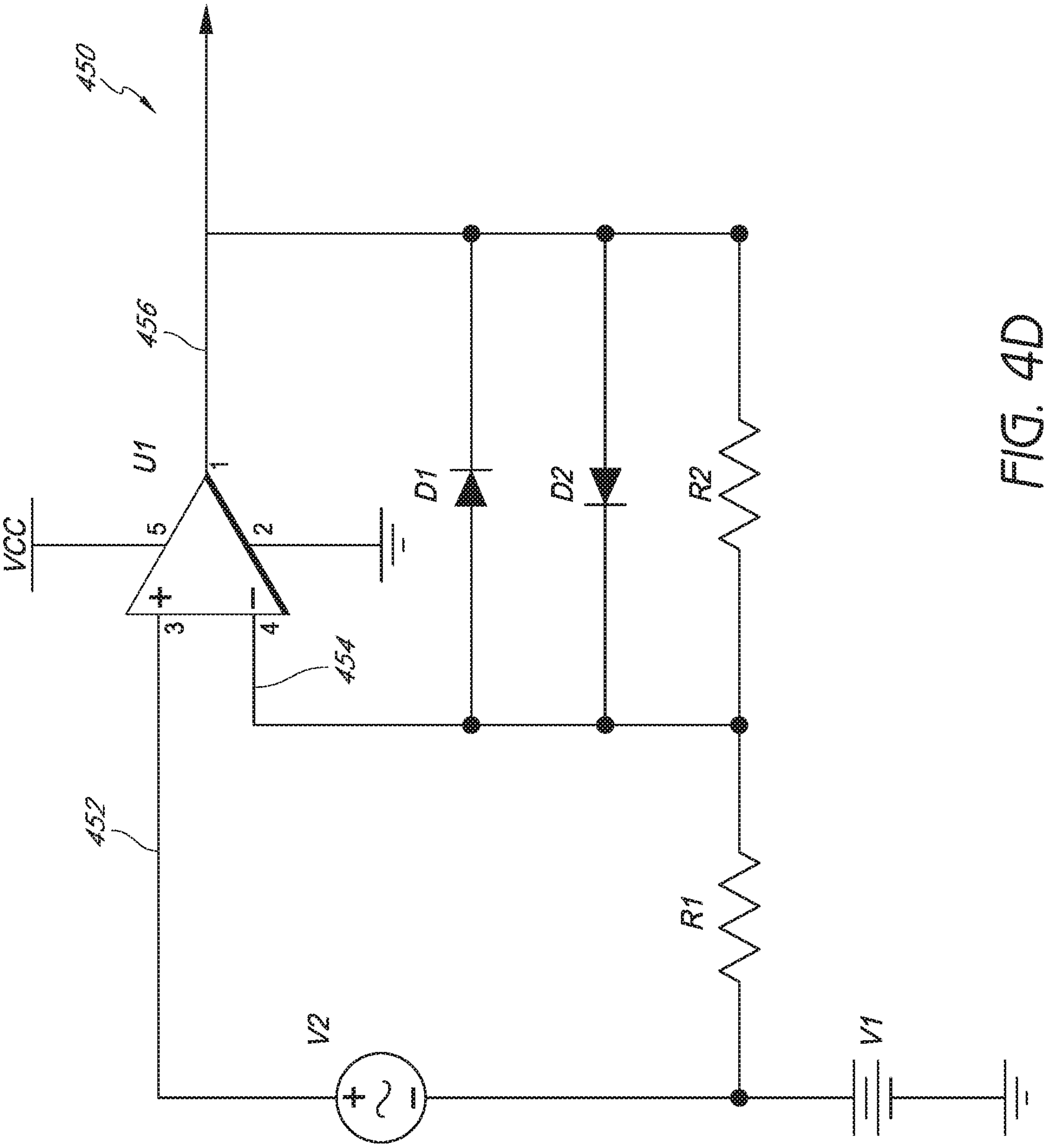
FIG. 4D illustrates a diagram of an example circuit configured to perform dynamic range compression according to one embodiment.
Figure 5:
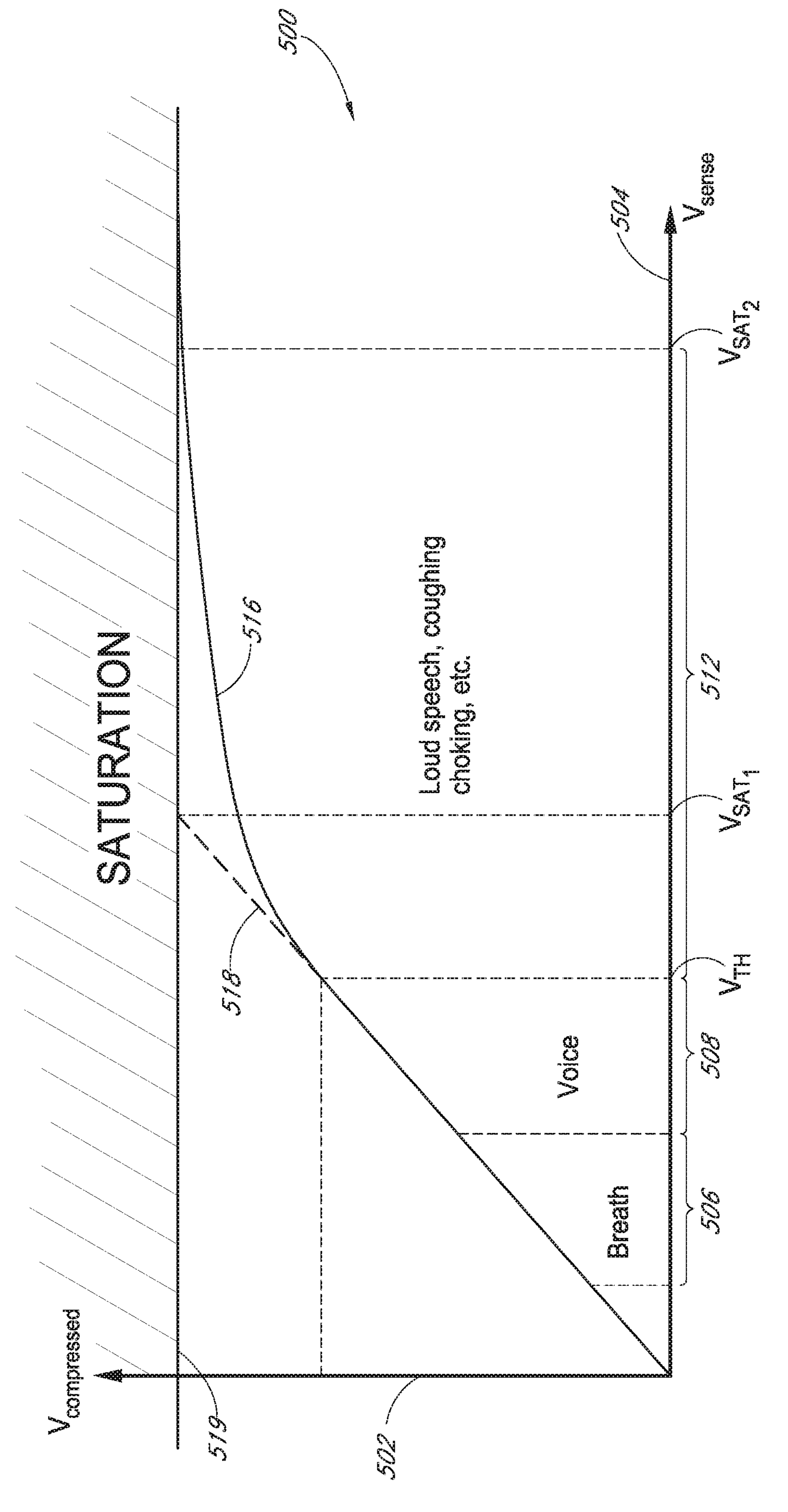
FIG. 5 graphically illustrates a dynamic range compression function implemented by an example sensor according to embodiments of the disclosure.

Referring to the drawings, FIGS. 1A-B, 2 and 12 illustrate example patient monitoring systems, sensors, and cables that can be used to provide acoustic physiological monitoring of a patient, such as respiratory monitoring. FIGS. 4-5 illustrate embodiments of sensors, systems and related techniques capable of improving the operable range of captured physiological sound signals. FIGS. 6A-9 illustrate embodiments of sensors and systems employing multiple sensing elements and/or sensors to provide an improved signal-to-noise ratio according to certain embodiments. Additionally, FIGS. 10A-11 illustrate embodiments of active acoustic sensors. Embodiments of FIGS. 3-11 can be implemented at least in part using the systems and sensors described in FIGS. 1A-1B, 2 and 12.

Figure 1A:
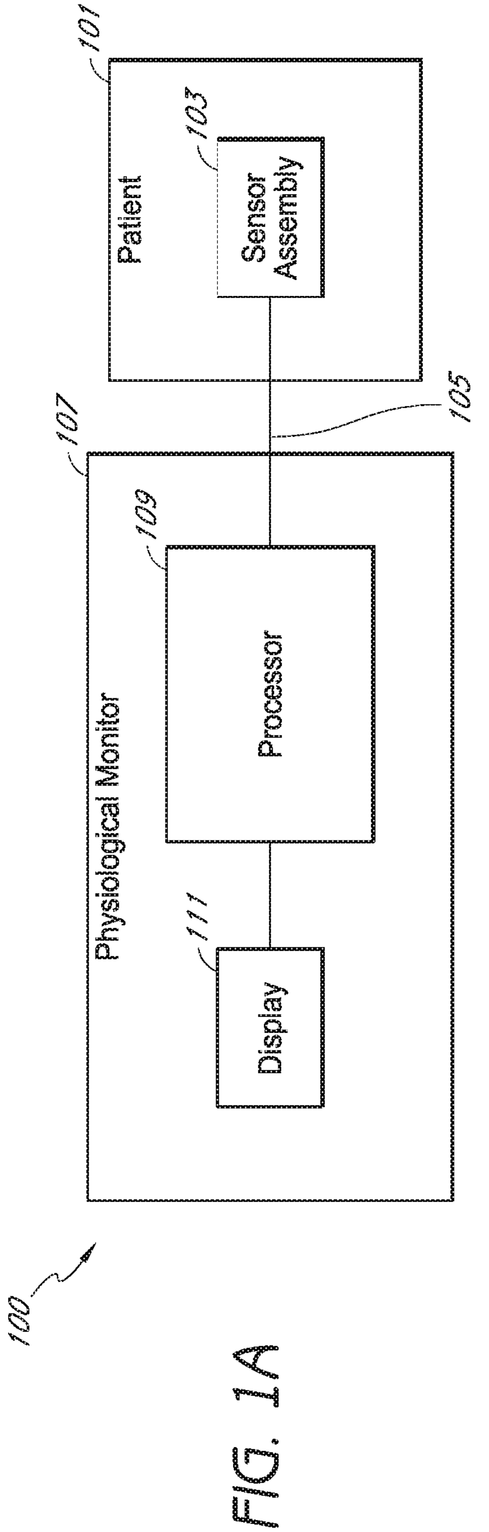
FIGS. 1A-B are block diagrams illustrating physiological monitoring systems in accordance with embodiments of the disclosure.

FIG. 1A illustrates an embodiment of a physiological monitoring system 100. A medical patient 101 is monitored using one or more sensor assemblies 103, each of which transmits a signal over a cable 105 or other communication link or medium to a physiological monitor 107. The physiological monitor 107 includes a processor 109 and, optionally, a display 111. The one or more sensors 103 include sensing elements such as, for example, acoustic piezoelectric devices, electrical ECG leads, or the like. The sensors 103 generate respective signals by measuring a physiological parameter of the patient 101. The signal is then processed by one or more processors 109. The one or more processors 109 then communicate the processed signal to the display 111. In an embodiment, the display 111 is incorporated in the physiological monitor 107. In another embodiment, the display 111 is separate from the physiological monitor 107. In one embodiment, the monitoring system 100 is a portable monitoring system. In another embodiment, the monitoring system 100 is a pod, without a display, that is adapted to provide physiological parameter data to a display.

In some embodiments, the monitor 107 includes a communication module (not shown) that allows the raw sensor signal and/or a processed signal to be communicated to another device. For example, a communications module can wirelessly transmit sensor signal information over a network for remote processing by a remote processing system. In some embodiments, the monitor includes only a communications module.

For clarity, a single block is used to illustrate the one or more sensors 103 shown in FIG. 1A. It should be understood that the sensor 103 block shown is intended to represent one or more sensors. In an embodiment, the one or more sensors 103 include a single sensor of one of the types described below. In another embodiment, the one or more sensors 103 include at least two acoustic sensors. In still another embodiment, the one or more sensors 103 include at least two acoustic sensors and one or more ECG sensors. In each of the foregoing embodiments, additional sensors of different types are also optionally included. Other combinations of numbers and types of sensors are also suitable for use with the physiological monitoring system 100.

In some embodiments of the system shown in FIG. 1A, all of the hardware used to receive and process signals from the sensors is housed within the same housing. In other embodiments, some of the hardware used to receive and process signals is housed within a separate housing. In addition, the physiological monitor 107 of certain embodiments includes hardware, software, or both hardware and software, whether in one housing or multiple housings, used to receive and process the signals transmitted by the sensors 103.

Figure 1B:
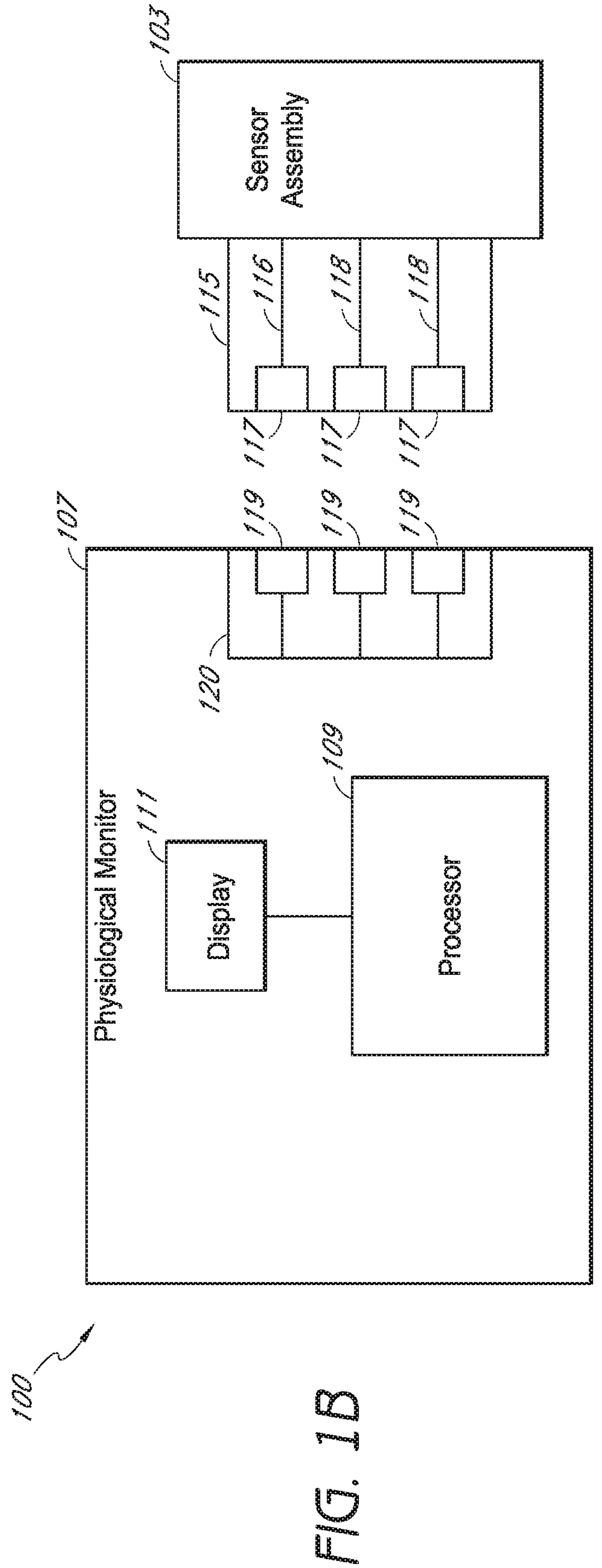

As shown in FIG. 1B, the acoustic sensor assembly 103 can include a cable 115 or lead. The cable 115 typically carries three conductors within an electrical shielding: one conductor 116 to provide power from the physiological monitor 107, one conductor 118 to provide a ground signal from the physiological monitor 107, and one conductor 118 to transmit signals from the sensor 103 to the physiological monitor 107. In some embodiments, the ground signal is an earth ground, but in other embodiments, the ground signal is a patient ground, sometimes referred to as a patient reference, a patient reference signal, a return, or a patient return. In some embodiments, the cable 115 carries two conductors within an electrical shielding layer and the shielding layer acts as the ground conductor. Electrical interfaces 117 in the cable 115 enable the cable to electrically connect to electrical interfaces 119 in a connector 120 of the physiological monitor 107. In another embodiment, the sensor assembly 103 and the physiological monitor 107 communicate wirelessly.

Additional information relating to acoustic sensors compatible with embodiments described herein, including other embodiments of interfaces with the physiological monitor, are included in U.S. patent application Ser. No. 12/044,883, filed Mar. 7, 2008, entitled "Systems and Methods for Determining a Physiological Condition Using an Acoustic Monitor," (hereinafter referred to as "the '883 Application"), U.S. Provisional Application No. 61/141,584, entitled "Acoustic Sensor Assembly", (hereinafter referred to as "the '584 Application"), filed Dec. 30, 2008, U.S. patent application Ser. No. 12/643,939, entitled "ACOUSTIC SENSOR ASSEMBLY," filed on Dec. 21, 2009, (hereinafter referred to as "the '939 Application"), and U.S. patent application Ser. No. 12/904,931, entitled "ACOUSTIC RESPIRATORY MONITORING SENSOR HAVING MULTIPLE SENSING ELEMENTS," each of which is incorporated in its entirety by reference herein.

Figure 2:
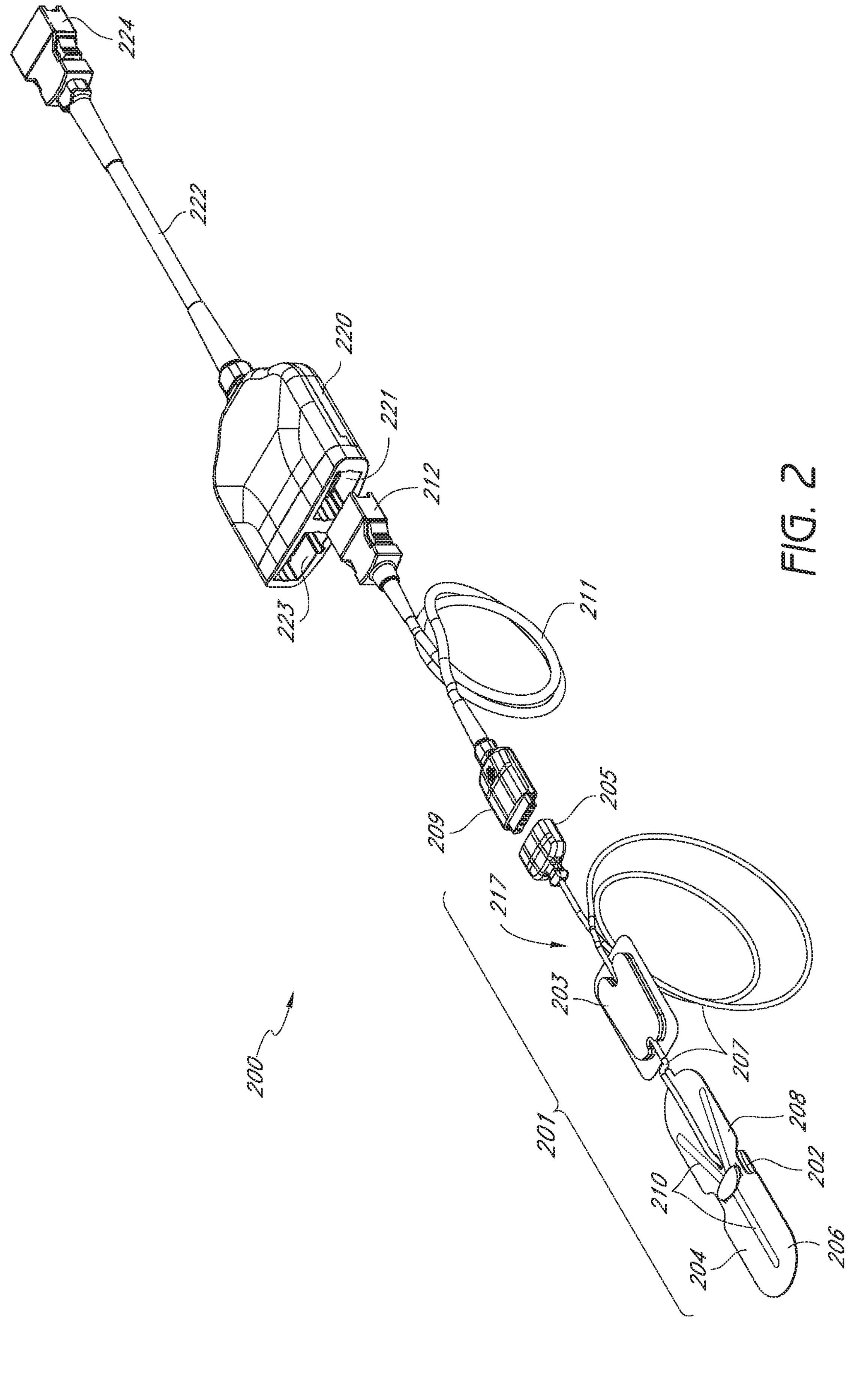
FIG. 2 is a top perspective view illustrating portions of a sensor system in accordance with an embodiment of the disclosure.

FIG. 2 illustrates an embodiment of a sensor system 200 including a sensor 201 suitable for use with any of the physiological monitors shown in FIGS. 1A and 1B. The sensor system 200 includes a sensor 201, a sensor cable 217, a patient anchor 203 attached to the sensor cable 217, and a connector 205 attached to the sensor cable 217. The sensor 201 includes a shell 202 configured to house certain componentry of the sensor 201, and an attachment subassembly 204 positioned the sensor 201 and configured to attach the sensor 201 to the patient.

The sensor 201 can be removably attached to an instrument cable 211 via an instrument cable connector 209. The instrument cable 211 can be attached to a cable hub 220, which includes a port 221 for receiving a connector 212 of the instrument cable 211 and a second port 223 for receiving another cable. In certain embodiments, the second port 223 can receive a cable connected to a pulse oximetry or other sensor. In addition, the cable hub 220 could include additional ports in other embodiments for receiving additional cables. The hub includes a cable 222 which terminates in a connector 224 adapted to connect to a physiological monitor (not shown). In another embodiment, no hub is provided and the acoustic sensor 201 is connected directly to the monitor, via an instrument cable 211 or directly by the sensor cable 217, for example.

The component or group of components between the sensor 201 and the monitor in any particular embodiment may be referred to generally as a coupling apparatus. For example, where one or more of the following components are included, such components or combinations thereof may be referred to as a coupling apparatus: the sensor cable 217, the connector 205, the cable connector 209, the instrument cable 211, the hub 220, the cable 222, and/or the connector 224. It should be noted that one or more of these components may not be included, and that one or more other components may be included between the sensor 201 and the monitor, forming the coupling apparatus.

The acoustic sensor 201 can further include circuitry for detecting and transmitting information related to biological sounds to the physiological monitor. These biological sounds can include heart, breathing, and/or digestive system sounds, in addition to many other physiological phenomena. The acoustic sensor 201 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 Application). In other embodiments, the acoustic sensor 201 is a biological sound sensor such as those described in U.S. Pat. No. 6,661,161 or U.S. patent application Ser. No. 12/643,939, filed on Dec. 21, 2009 (the '939 Application), both of which are incorporated by reference herein in their entirety. Other embodiments include other suitable acoustic sensors.

In an embodiment, the acoustic sensor 201 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can generate a voltage potential across the electrical poles that is responsive to vibrations generated by the patient.

The shell 202 according to certain embodiments houses a frame (not shown) configured to support various components of the sensor 201. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 202 can include an acoustic coupler not shown), which advantageously improves the coupling between the source of the signal to be measured by the sensor (e.g., the patient's body) and the sensing element. The acoustic coupler of one embodiment includes a bump positioned to apply pressure to the sensing element so as to bias the sensing element in tension. For example, the bump can be positioned against the portion of the sensing element that is stretched across the cavity of the frame.

The attachment sub-assembly 204 in some embodiments includes first and second elongate portions 206, 208. The first and second elongate portions 206, 208 can include patient adhesive (e.g., in some embodiments, tape, glue, a suction device, etc.). The adhesive on the elongate portions 206, 208 can be used to secure the sensor subassembly 202 to a patient's skin. One or more resilient backbone members 210 included in the first and/or second elongate portions 206, 208 can beneficially bias the sensor subassembly 202 in tension against the patient's skin and/or reduce stress on the connection between the patient adhesive and the skin.

While an example sensor system 200 has been provided, embodiments described herein are compatible with a variety of sensors and associated components. For example, compatible acoustic couplers, support frames, attachment subassemblies, sensing elements, and other components are described with respect to FIGS. 19-23 below and in the '939 Application.

Figure 3:
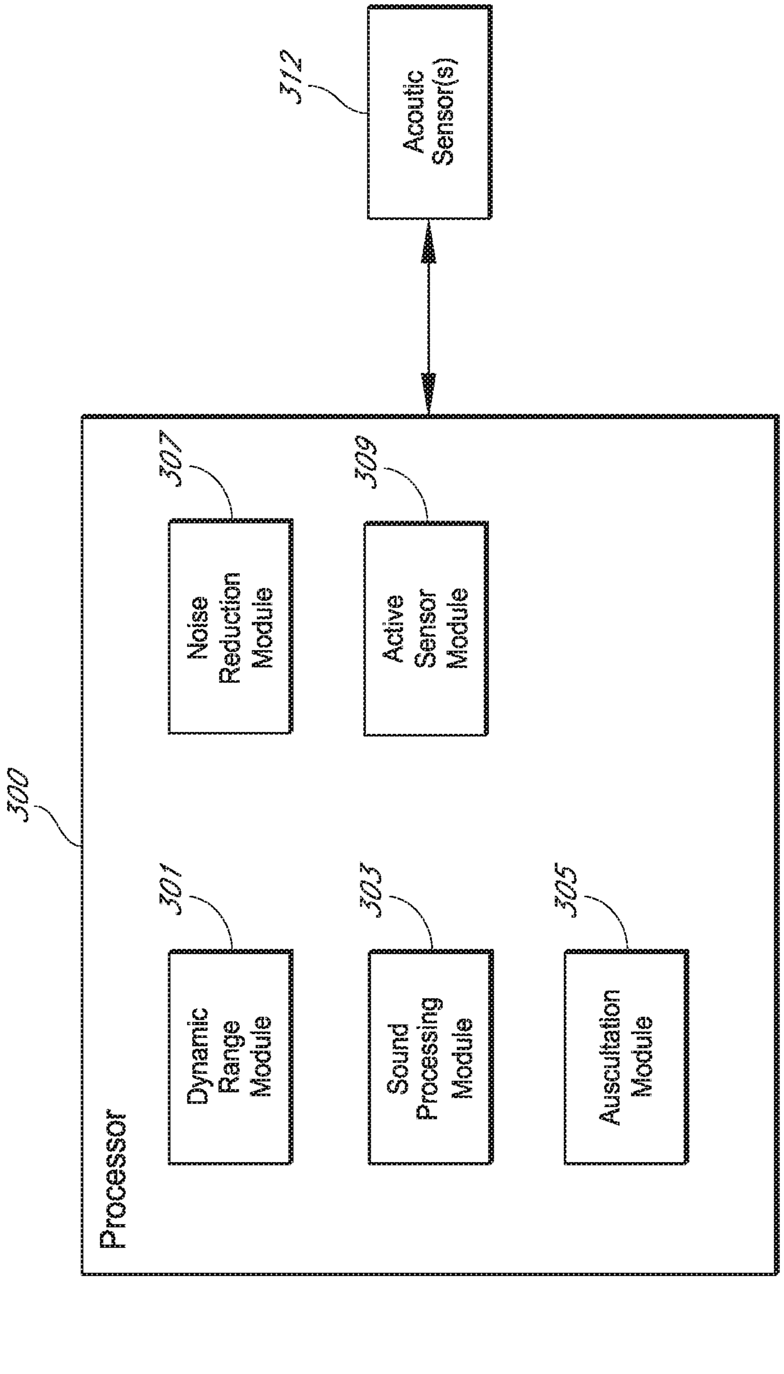
FIG. 3 is a block diagram illustrating a processor of a physiological monitoring system having a plurality of modules implemented thereon according to embodiments of the disclosure.

FIG. 3 is a block diagram illustrating a processor 300 of a physiological monitoring system. The processor 300 communicates with at least one acoustic sensor 312. In certain embodiments, the processor 300 includes one or more of a dynamic range module 301, a sound processing module 303, an auscultation module 305, a noise reduction module 307, and an active sensor module 309.

One or more of the modules are not included in certain embodiments, and any of the individual modules by themselves or any combination of modules can be included. The monitoring system, processor 300, and acoustic sensor(s) 312 may be any of those described herein such as the physiological monitor 100, processor 109, and sensor assembly (or assemblies) 103 of FIGS. 1A-1B, the sensor system 200, sensor 201 and monitor of FIG. 2, the sensor system 1200, sensor 1201 or monitor of FIG. 12, or some other monitoring system, processor and/or sensor assembly, respectively.

As described above, in patient monitoring situations, acoustic sensors can be subject to a very wide spectrum of bodily and other sounds. For example, some bodily sounds, such as breathing and other respiratory sounds may be relatively quiet, corresponding to relatively small acoustical and corresponding electrical signal values. Other physiological sounds, such as loud speech sounds, coughing, choking, gasping, etc., on the other hand, correspond to much larger acoustical and corresponding electrical signal values. The acoustic sensor 312 can include a sensing element (e.g., a piezoelectric film) having a relatively wide input dynamic range, and is therefore capable of detecting relatively low intensity sounds and relatively high intensity sounds without reaching saturation or otherwise distorting. The sensing element can also have a large output dynamic range and thus be capable of producing a signal having a relatively large range of valid, un-distorted, output signal (e.g., voltage or current) values.

One or more subsequent components (e.g., a preamplifier) in the signal processing path, on the other hand, may have a smaller input dynamic range and thus only be capable of processing a smaller range of signal values before reaching saturation, clipping, or otherwise producing a distorted output value. For example, the preamplifier or other relatively low dynamic range component may be configured with a relatively high gain, which may cause saturation for a wider range of input signal values. To reduce losses in captured sound content caused by such saturation, the dynamic range module 301 of certain embodiments generally compresses the signal produced by the sensing element, or otherwise compresses the input signal received by the lower dynamic range component. The compressed signal is then provided to preamplifier or other component in the data path, thereby avoiding saturation for a desired range of sensed signal values, expanding the overall dynamic range of the sensor 300. For example, the ratio of the highest to lowest amplitude sound intensity values that the sensor system 300 can accurately process is increased according to such a technique. In additional embodiments, instead of or in addition to compressing the input to the lower dynamic range component, the output of the lower dynamic range component is compressed directly. Dynamic range improvement is discussed in further detail below with respect to the embodiments of FIGS. 4 and 5.

Such techniques can be useful in a variety of contexts, particularly when relatively loud physiological sounds are expected, such as for voice processing applications or in emergency situations or other situations where it can be beneficial to identify sounds that differ in frequency, amplitude or intensity from the sounds typically sensed by an acoustic sensor. For example, sounds such as coughing, choking, gasping, etc., can be indicative of situations in which intervention from medical personnel may be appropriate, and might not be otherwise detectable if the sensor were to saturate. Such sounds may also be indicative of noise in a respiratory signal. The improved or expanded range of physiological sounds that can be processed using the dynamic range module 301 can be useful in capturing such sounds, particularly where they are relatively loud, for processing.

The sound processing module 303 of certain embodiments accesses a library of sound signatures and compares the received signal with the entries in the library to characterize or identify sounds in the received signal. In another embodiment, the sound processing module 303 generates and/or accesses a library of sound signatures specific to the patient, or specific to a particular type of patient (e.g., male/female, pediatric/adult/geriatric, etc.)

Samples from the patient may be recorded and used to generate the sound signatures. In some embodiments, certain signal characteristics are used to identify particular sounds or classes of sounds. For example, in one embodiment, signal deviations of relatively high amplitude and or sharp slope may be identified by the sound processing module 303. Sounds identified in various embodiments by the sound processing module 303 include, but are not limited to, breathing, speech, choking, swallowing, spasms such as larynx spasms, coughing, gasping, etc.

Once the sound processing module 303 characterizes a particular type of sound, the system 300 can, depending on the identified sound, use the characterization to generate an appropriate response. For example, the system 300 may alert the appropriate medical personnel, modify treatment, etc. In one embodiment, medical personnel may be alerted via an audio alarm, mobile phone call or text message, or other appropriate means.

In one example scenario, the breathing of the patient can become stressed or the patient may begin to choke due to saliva, mucosal, or other build up around an endotracheal tube. Muscle relaxant medication can be given to the patient to alleviate the stressed breathing or choking. In one embodiment, the sound processing module 303 can identify the stressed breathing sounds indicative of such a situation and cause a dosage of muscle relaxant medication to be automatically administered to the patient, or can alert medical personnel to the situation.

Achieving an improved operable range of physiological sounds and/or providing sound processing techniques such as those described above can also be beneficially employed in situations where it is useful to communicate bodily sound information using acoustic sensors. For example, in certain circumstances, it can be useful to communicate bodily sounds (e.g., respiratory sounds, heart sounds, voice sounds, etc.) or bodily sound information derived therefrom.

In certain embodiments, for example, the auscultation module 305 may process the signal received by the acoustic sensor 312 and provide an audio output (e.g., auscultatory output) indicative of internal body sounds of the patient, such as heart sounds, breathing sounds, gastrointestinal sounds, and the like. In some embodiments the auscultation module 305 allows medical personnel to remotely listen (e.g., using a headset or speakers) to bodily sounds for patient diagnosis, communication, etc. For example, medical personnel may listen to the audio output in a different room in the hospital than the patient's room, in another building, etc. The audio output may be transmitted wirelessly (e.g., via Bluetooth, IEEE 802.11, over the Internet, etc.) in some embodiments such that medical personnel may listen to the audio output from generally any location.

The monitoring system 300 may also be capable of recording sounds processed by the auscultation module 305 for later playback or analysis, providing improved diagnostic capability and user flexibility. Additionally, the acoustic sensors described herein according to certain embodiments are generally sanitized prior to each use or may be pre-sanitized, single-use sensors. As such, the audio output functionality described herein may be provide enhanced sanitation as compared to other mechanisms available for listening to bodily sounds (e.g., acoustic stethoscopes) which may become soiled after repeated use. In other embodiments, sensors described herein may capable of other beneficial functions such as sound recognition, patient communication, and the like. Additionally, the auscultation module 305 can remove the need for a separate auscultatory device, reducing the number of instruments involved in patient monitoring.

In certain embodiments, the auscultatory module 305 allows medical personnel to remotely monitor bodily sounds of the patient. For example, the monitoring system 300 may allow for remote communication with a medical personnel through a listening device (e.g., via cell phone, custom headset, etc.) such that the medical personnel can listen to the bodily sounds of the patient processed by the auscultation module 305.

Additional embodiments of systems employing auscultatory and/or sound processing techniques, or which are capable of providing other related functionality, can be found in U.S. application Ser. No. 12/905,036, entitled PHYSIOLOGICAL ACOUSTIC MONITORING SYSTEM, filed on Oct. 14, 2010, which is hereby incorporated by reference in its entirety herein.

In certain circumstances, acoustical noise such as ambient or environmental sounds can significantly reduce the quality of physiological measurements obtained by the monitoring system 300. Where the monitoring system 300 includes a plurality of sensors 312 or sensing elements, the noise reduction module 307 can be configured to beneficially process the measurement output of a plurality of acoustic sensors 312 attached to a medical patient at a plurality of measurement sites so as to generate an enhanced (e.g., noise reduced) measurement.

The noise reduction module 307 may operate to lower acoustical noise level and/or provide the sensor system 300 with improved noise immunity. The noise reduction module 307 may produce a noise-reduced measurement having an improved signal to noise ratio, for example. In some embodiments, the noise reduction module 307 generates the noise-reduced signal by beneficially employing knowledge of phase relationships (1) between the noise (e.g., ambient noise) components of the acoustic signals received by the sensors and (2) between the components of the acoustic signals received by the sensors indicative of a physiological sounds (e.g., internal bodily sounds indicative of a respiratory sounds).

The noise reduction module 307 may employ a cross-correlation technique in certain embodiments to generate the noise-reduced signal. Example noise reduction systems and methods compatible with the noise reduction module 307 are described herein with respect to FIGS. 6A-9.

Acoustic sensors 312 may be attached to a variety of locations on the patient. The tissue at each location may have specific tissue acoustical characteristics. Knowledge of such characteristics may be useful in monitoring, diagnosis, and/or sensor calibration. Moreover, sensors 312 may be improperly attached or the connection between the sensor and the patient may otherwise be compromised, such as due to yanking or jerking on the sensor 312 or sensor cable. The active sensor module 309 of some embodiments is configured to cause the acoustic sensor 312 to transmit vibrations into the medical patient, receive vibrations coming from the patient in response to the transmitted vibrations, and intelligently process the received signals to determine one or more parameters.

In such embodiments, the active sensor module 309 enables enhanced functionality of the sensor system 300 in addition to measuring physiological parameters. For example, an acoustic signal can be transmitted into the patient and the vibrational response can be measured so as to characterize the tissue to which the sensor is attached, determine the integrity of the mechanical connection between the sensor and measurement site, or for other purposes. Such information can advantageously be used for sensor calibration, alerting medical personnel (e.g., to probe-off conditions), and the like. Example active sensor modules and methods thereof are described herein with respect to FIGS. 10-11, for example.

While each of the dynamic range module 301, sound processing module 303, auscultation module 305, noise reduction module 307 and active sensor module 309 are shown implemented as software modules running on the processor 307, other configurations are possible. For example, one or more of the modules or components thereof may be implemented in hardware, such as in custom circuitry, programmable logic (e.g., in a programmable logic array), or in an application-specific integrated circuit(s). In some embodiments, the modules or components there of are implemented across multiple processors. In one embodiment, the modules are remotely implemented on one or more processors in communication with the physiological monitor 300 over a network.

Dynamic Range Improvement

FIG. 4 is a schematic diagram of one embodiment of a sensor system 400 including a sensor 401 coupled to a patient 403, and a physiological monitor 409 in communication with the sensor 401. The system 400 generally includes componentry enabling the system 400 to process a wider dynamic range of sound intensity values.

The illustrated sensor 401 includes a sensing element 408, a compression module 402, and front-end componentry 404. The monitor 409 includes one or more processors 416, and can include a decompression module 418. The monitor is generally configured to process the signal 412 received from the sensor 401, and in some embodiments is configured determine, display, or otherwise output, one more physiological parameters (e.g., respiratory rate, heart rate, etc.) of the patient as described herein. The monitor 409 and sensor 401 can generally be any of the sensors described herein, for example, such as any of the sensors or monitors described above with respect to FIGS. 1-3 and 6-12 or incorporated by reference herein. The monitor 409 according to various embodiments can include one or more acoustic front-ends, analog to digital converters, a digital signal processor (DSP), and the like. The DSP can comprise a wide variety of data and/or signal processors capable of executing programs for determining physiological parameters from input data.

As is described herein, the compression module 402 and/or decompression module 418 generally work together to improve the dynamic range of the sensor 401 so as to widen the range of physiological sound content that can be accurately processed by the sensor 401. Thus, the compression module 402 and/or decompression module 418 can be referred to as a dynamic range module and can be included in the dynamic range module 301 of FIG. 3, for example.

The front-end componentry 404 is shown and described with respect to the illustrative embodiment and other embodiments herein as a separate component from the compression module 402. However, in other embodiments, the compression module 402 and the front-end componentry 404 or portions thereof can be arranged differently with respect to one another. For example, the compression module 402 and front end componentry 404 can be arranged in a feed-back and/or feed-forward arrangement, examples of which are shown in FIGS. 4B-4D, discussed below. Moreover, the compression module and the front-end 404 componentry or a subset thereof may form the same circuit in some embodiments. For example, in one embodiment, the front-end componentry 404 includes a preamplifier circuit configured both to compress the sensed signal 407 according to compression techniques described herein and also preamplify the signal 407.

An illustrative example embodiment will now be described. The example embodiment, the sensing element 408 is a piezoelectric film having a relatively high input dynamic ranges, and is wrapped around a frame in tension as described above with respect to the sensor 201 of FIG. 2. The sensing element 408 detects an acoustic signal 405 (e.g., physiological sounds) from the patient 403 and produces a corresponding electrical signal 407 (e.g., a voltage signal). The sensing element 408 has a relatively large output dynamic range, and the signal 407 thus has a relatively large range of possible un-distorted values. For example, the output dynamic range may be relatively larger than a subsequent component in the sensor data path, such as a preamplifier, as described below.

In certain embodiments, the preamplifier and/or other front-end componentry 404 generally decouple the power supply (not shown) and performs preliminary signal processing. The front-end componentry 404 can include clamping diodes to provide electrostatic discharge (ESD) protection and a mid-level voltage DC offset for the piezoelectric signal to ride on, to be superimposed on or to be added to. The front-end componentry 404 may include a preamplifier circuit residing in one embodiment to provide gain to the sensed signal. The front-end componentry 404 may also have a high pass filter to eliminate unwanted low frequencies such as below about 100 Hz for breath sound applications, and an op amp to provide gain to the piezoelectric signal. The front-end componentry 404 may have a low pass filter at the output of the preamplifier to filter out unwanted high frequencies. In an embodiment, a high pass filter is provided on the output in addition to or instead of the low pass filter. The front-end componentry 404 may also provide impedance compensation to the signal, such as a series/parallel combination used to control the signal level strength and frequency of interest that is input to the preamplifier. IN one embodiment, the impedance compensation is used to minimize variation in the sensed signal. The impedance compensation can be constructed of any combination of resistive, capacitive and inductive elements, such as RC or RLC circuits. In some embodiments, the preamplifier can be configured to amplify a relatively low level detected signal to a line-level signal 412 for transmitting to the monitor 409 over a cable (not shown). As described, the preamplifier and/or other front-end componentry can additionally or alternatively be configured to balance reduce signal impedance before transmitting the signal over the cable, reduce system noise by introducing signal gain before one or more noisy stages in the data path, or a combination thereof. The preamplifier in the example embodiment is capable of processing a relatively smaller input dynamic range than the output dynamic range of the sensing element 408. Thus, the differential range of input voltage signals the preamplifier can process without producing a distorted output is smaller than the differential range of output signals produced by the sensing element 408. Thus, without dynamic range compression, the preamplifier would saturate for certain values of the signal 407 falling in the output dynamic range of the piezoelectric film 408.

To reduce undesirable losses in sound content due to such saturation or other distortion, the compression module 402 according to the example produces a signal 410 corresponding to a compressed version of the sensed signal 407. The compression scheme may be selected based on the input dynamic range of the preamplifier, for example. A plot 500 showing values of a compressed signal generated by a compression module 402 is shown in FIG. 5. Referring now to FIGS. 4 and 5, the plot 500 shows compressed signal 410 values (axis 502) generated by the compression module 402 for given signal values 407 (axis 504) produced by the sensing element 408. Signal values above the line 519 will cause the preamplifier to saturate or otherwise produce a distorted output.

The linear portion of the compressed signal 410 curve along the dotted line 518 corresponds to values of the sensed signal 407 falling below a threshold sensed signal 407 voltage ($V_{TH}$). According to the example embodiment, the compression module 402 does not compress the sensed signal 407 for values below $V_{TH}$ and the signal 410 thus corresponds to an unmodified version of the signal 407 for such values. Passing an unmodified version of the input signal for at least some sensed signal 407 values can advantageously preserve resolution in the sound content corresponding to such values, as is described in more detail below.

As indicated by the dotted line 518, if the compressed signal 410 is presented to the preamplifier as an unmodified version of the sensed signal 407 for signal 407 values above $V_{SAT1}$, the preamplifier will saturate. Thus, the compression module 402 produces a compressed version of the sensed signal 407 for signal 407 values above $V_{TH}$, as illustrated by the curve 516. The compression module 402 of the example embodiment performs a logarithmic function on the sensed signal 407. For example, the compression module includes a logarithmic amplifier configured to produce a compressed or otherwise reduced or attenuated signal 410 according to the curve 516. A wide variety of other compression schemes can be employed in other embodiments, as will be described below.

As shown, compressed signal values 410 along the curve 516 generally gradually approach the preamplifier saturation region. Thus, the compressed signal 410 reaches saturation for an input voltage value $V_{SAT2}$ which is significantly higher than $V_{SAT1}$, without compression. As such, the preamplifier generally will operate without saturating or otherwise distorting for a wider range of sensed signal 407 values, improving the overall dynamic range of the sensor 400.

As shown, certain characteristic bodily sounds may generally correspond to various regions of the plot 500. For example, in one embodiment, sensed signal 407 values falling in the regions 506, 508 generally correspond to breathing and typical voice sounds, while sensed signal 407 values falling in the region 512 correspond to relatively louder sounds such as loud speech, snoring coughing, choking, and/or other higher volume physiological sounds. As shown, in the example embodiment, use of the compression module 402 advantageously avoids preamplifier saturation for a wider range of sensed signals 407 corresponding to relatively louder sounds in the region 512.

Due to the compression, the signal received by the monitor 409 can include distortive effects, and the decompression module 418 is generally configured to remove or reduce such distortive effects. In the example embodiment, the decompression module 418 includes a software module executing on the processor 416 of the monitor 409, and is configured to perform the mathematical inverse of the function performed by the compression module 402. Other de-compression techniques are possible, and some are described below.

While described with respect to the above example for clarity, the implementation of the various components of the system can vary. For example, FIGS. 4B-4C show example alternative arrangements in which a compression module 402 is arranged in feed-back and feed-forward relationships with respect to the front-end componentry, respectively. In the feed-back configuration of FIG. 4B, the compression module 402 generally compresses the input to the front-end componentry 404 (e.g., the sensing element output signal) in response to front-end componentry 404 output. In a feed-forward configuration, the compression module 402 compresses the output of the front-end componentry rather than compressing the input. In some embodiments, a combination of feed-back and feed-forward configurations are used.

FIG. 4D illustrates a diagram of an example circuit 450 configured to perform dynamic range compression according to one embodiment. The circuit 450 includes an operational amplifier U1 arranged in a non-inverting, differential configuration with a pair of resistors R1, R2. For the purposes of illustration, the circuit 450 is shown as including an AC voltage source V2 biased by a DC offset voltage V1. In some embodiments, the AC voltage source 420 is representative of the electrical output of a sensing element (not shown). Thus, the signal 452 is representative of the sensing element output signal or a signal derived therefrom.

The operational amplifier U1 and resistors R1, R2 generally form a preamplifier circuit configured to pre-amplify the sensing element signal 452. For example, in one embodiment, the preamplifier has a gain of two and produces a pre-amplified signal 456 which is generally double the input signal, although a multitude of other preamplifier configurations are possible. However, as described herein, the preamplifier may have a relatively low dynamic range and may saturate for certain desired values of the input signal 452.

To improve the dynamic range of the preamplifier, a compression module including a pair of diodes D1, D2 connected between the output of the operational amplifier U1 (which is also the preamplifier output) and the non-inverting input of the operational amplifier U1. As shown, the diodes D1, D2 are connected in parallel and in opposite polarity with respect to one another. Generally speaking, the compression module including the two diodes D1, D2 compresses the preamplifier output when the output signal 456 falls within certain predetermined ranges. For example, in one embodiment, when the output signal 456 is greater than a first threshold value, the compression module compresses the output signal 456, reducing the effective gain of the preamplifier from two to one. Conversely, when the output signal 456 is less than a second threshold value, the compression module reduces the gain of the output signal 456 from two to one. A variety of threshold values are possible. For example, where the output signal 456 is an AC signal that is positively biased by a DC offset, the first and second threshold values may be selected generally symmetrically about the DC offset such that compression occurs symmetrically with respect to the positive and negative signal peaks. In other embodiments, where the output signal 456 is an AC signal that alternates between positive and negative values, the threshold values may comprise positive and negative values of equal magnitude, respectively. In other embodiments, asymmetric threshold values can be used, or only one peak of the AC signal is compressed.

Referring again to FIG. 4A, depending on the desired compression scheme, the compression module 402 can be configured to perform a wide variety of functions on the sensed signal 407. For example, the compression module 402 can implement one or more of a variety of linear functions (e.g., scalar functions), logarithmic functions, or other types of linear, non-linear functions, or combinations thereof. In some embodiments, the function implemented by the compression module 402 corresponds to a polynomial function having a set of corresponding coefficients and/or an offset. In one embodiment, the function is a third order polynomial, although other order polynomials can be used.

Generally, the amount or quality of compression used can be selected based on a trade-off between the compression achieved and the resolution of the sensed signal that is preserved. For example, in the example shown in FIG. 5, signal values corresponding to breathing and voice sounds are uncompressed, thereby preserving resolution with respect to those sounds. On the other hand, signal values corresponding to louder sounds are compressed, resulting in a loss of resolution, but an increase in the range of such sounds that can be captured. Because breathing and voice sounds are relatively low intensity, it can be beneficial to maintain resolution to more readily distinguish fluctuations in sound levels (e.g., for physiological monitoring or remote listening purposes). The compression scheme of FIG. 5 advantageously allows for preserves resolution for quieter sounds while still allowing louder sounds to be processed.

In other embodiments, the compression module 402 compresses the signal 407 for all sensed signal 407 values, thereby further increasing the overall dynamic range of the sensor. In such cases, the compression module 402 may implement only one function for all sensed signal 407 values, or may implement a first function for signal values below a threshold voltage, and a second function for values at or above the threshold. In other embodiments, three, four or more functions and corresponding thresholds can be used. In one embodiment, the compression is generally piece-wise linear, and the compression module 402 compresses the signal 407 according to a first slope when the signal exceeds a first threshold and compresses the signal 407 according to a second slope when the signal exceeds a second threshold value, and so forth. The term “multi-stage compression” may refer to embodiments where more than one function or curve is applied for different input signal value ranges.

Depending on the embodiment and corresponding compression scheme, the compression module 402 can include a variety of circuitry, including one or more amplifiers (e.g., operational amplifiers), comparators, multiplexors, combinations of the same and the like. The amplifier circuits can include linear (e.g., scalar), non-linear, logarithmic amplifiers, etc.

In various embodiments, the sensing element 408 can include generally any acoustic transducer or other type of acoustic sensing device, such as any of those described herein.

The front-end componentry 404 may include one or more additional components instead of, or in addition to a preamplifier. For example, the front-end componentry 404 can generally include any circuitry or other componentry configured condition the signal for later processing. Such circuitry can include analog circuitry such as one or more operational amplifiers, filters (e.g., high, low or bandpass filter), analog to digital converters, diodes, combinations of the same or the like. Moreover, where the front-end componentry 404 includes multiple components, any of the components can receive the compressed signal 410.

Moreover, the arrangement of the components shown residing on the sensor 400 may physically reside at some other location. For example, one or more of the components of the compression module 402 and/or front end componentry 404 can reside at some intermediate location (e.g., a cable, connector or hub) between the sensor 400 and the monitor 409, or can reside on the monitor 409 itself. In one embodiment, the compression module 402 is coupled to some other component in the sensor data path not residing in the front end 404.

Also, while not shown for the purposes of clarity, in certain configurations a variety of other circuitry or other componentry may be interposed between, or be otherwise connected to the various components. Moreover, the relative order of the compression module 402 and other components can be swapped or otherwise rearranged. For example, in one embodiment, the front-end componentry 404 includes multiple stages, and the compression module 402 resides between two of the stages. In another embodiment, multiple compression modules 402 reside between appropriate components in the data path.

While the signal 407 is referred to herein as the sensed signal 407 and is shown as being received by the compression module 402 directly from the sensing element 408 for the purposes of illustration, the signal 407 in certain embodiments is modified by one or more components disposed between the sensing element 408 and the compression module 402. In a similar fashion, the sensing element signals of FIGS. 4B-4C and the signal 452 of FIG. 4D may be modified by one or more other components before reaching the respective front-end componentry and/or compression module.

As described, the decompression module 418 receives the conditioned signal 412 and is configured to generally remove distorting effects introduced by the compression or modification process. In certain embodiments, the decompression module 418 has a very high numerical dynamic range and can thus numerically represent, without saturation, the uncompressed or otherwise unaltered signal 407 produced by the sensing element 408. While described in the above example as performing the mathematical inverse of the compression function, in some cases, the decompression module 418 does not perform the exact inverse of the function performed by the compression module 402. Instead, the decompression module 418 can perform some function approximating or otherwise based on or derived from the inverse, or otherwise generally reversing the compression.

For example, in some embodiments, coefficients of a polynomial representation of the compression function are stored in one or more memory devices. The decompression module 418 retrieves the coefficients and uses them to reconstruct the generally unaltered, pre-compressed sensed signal 907. A third order polynomial is used in one embodiment. In such an embodiment, the decompression module 418 retrieves three coefficients and/or an offset value stored in an EPROM or other memory device and uses the values to decompress the signal.

As described, according to certain embodiments, the compressed signal 410 is generally a compressed version of the sensed signal 407, or portions thereof. Similarly, where the output of the front-end componentry 404 is directly modified, it is generally modified to generate a compressed version of the front-end output according to many of the embodiments described herein. Thus, the dynamic range modification is described generally throughout the disclosure as compression, dynamic range compression, and the like. However, in some cases, other forms of dynamic range improvement compatible with embodiments described herein do not involve compressing the sensed signal 407, or involve compressing for some signal values and not compressing for other signal values. In some embodiments, for example, a linear function (e.g., implementing a scalar multiplying factor) having a slope greater than one, or some other non-compressive function is implemented by the compression modules described herein. Moreover, while dynamic range improvement and compression is described in terms of signal magnitudes, in certain embodiments, other types of dynamic range improvement can be achieved. For example, the ratio of the highest and lowest acoustic frequencies that can be processed by the sensor system 400 can be improved according to certain compatible embodiments.

In some alternative embodiments, the sensor system 400 allows for the configuration or selection of the desired compression function. For example, depending on the desired application, a user may select from a plurality of modes implementing a variety of different functions. As one illustrative example scenario, a user may select a first mode implementing a first function suitable for relatively quiet conditions when the monitoring environment is relatively quiet. Conversely, the user may select a second mode implementing a second function suitable for relatively loud conditions when the monitoring environment is relatively loud. Modes and associated functions can be tailored for any number of situations, e.g., based on the type of physiological sound is being monitored, whether it is desirable to capture patient speech sounds, etc.

In other embodiments, the compression function or functions employed by the compression module 402 are automatically selected by the system 400 based on certain predetermined criteria. For example, while other criteria can be used, in one embodiment, the system 400 automatically changes the compression function when it detects a saturation condition or threshold number of saturation conditions at a relevant location or locations within the data path 401. The automatic selection can be based on an averaging or other operation performed on captured sound intensity values for a given period of time, on detection of a particular type or quality of detected sounds, such as the detection of speech sounds, or the like.

Additional Applications

According to some embodiments, acoustic sensors incorporating certain acoustical design advantages described herein can be used in an array of beneficial applications. Such applications described herein include enhanced monitoring of physiological parameters (e.g., respiratory parameters), auscultation (e.g., as described with respect to the auscultation module 305 of FIG. 3), sound characterization and identification (e.g., as described above with respect to FIG. 3), active sensor applications, etc.

Additionally, sensor systems of some embodiments are configured to be used as a microphone so as to allow for patient communication. For example, the sensor system may be adapted to transmit patient vocal communications to devices incorporating speakers, such as cell phones, walkie-talkies or other radio devices, remote patient monitors, etc. In one embodiment, appropriate medical personnel are equipped with such devices so that the patient can remotely communicate with them. For example, the patient monitor applies an appropriate filtering function to the signal received by the acoustic sensor in order to generate the audio output. In one embodiment, the acoustic sensor system includes a button on the sensor that allows the patient to activate the remote vocal communication functionality. In other configurations, a button may be located elsewhere to activate vocal communication, such as on the patient's bed, on the physiological monitor, etc. The button may alert a nurse or other medical personnel that the patient wants to communicate using the sensor, for example.

Such patient communication capability can allow for medical personnel to respond to emergency situations quickly and efficiently as compared to existing communication mechanisms such as button alarms which may not allow for voice communication and can be difficult for patient's to locate and operate, particularly in emergency situations. In some embodiments, the sensor can also be used as a speaker such that the medical personnel or others can remotely speak to the patient, thereby allowing for two-way communication.

The acoustic sensors described herein according to certain embodiments are generally sanitized prior to each use or may be pre-sanitized, single-use sensors. As such, the audio output functionality described herein may be provide enhanced sanitation as compared to other mechanisms available for listening to bodily sounds (e.g., acoustic or electronic stethoscopes) which may become soiled after repeated use. In other embodiments, sensors described herein may capable of other beneficial functions such as sound recognition, patient communication, and the like.

Noise Reduction Using Multiple Sensors

Figure 6A:
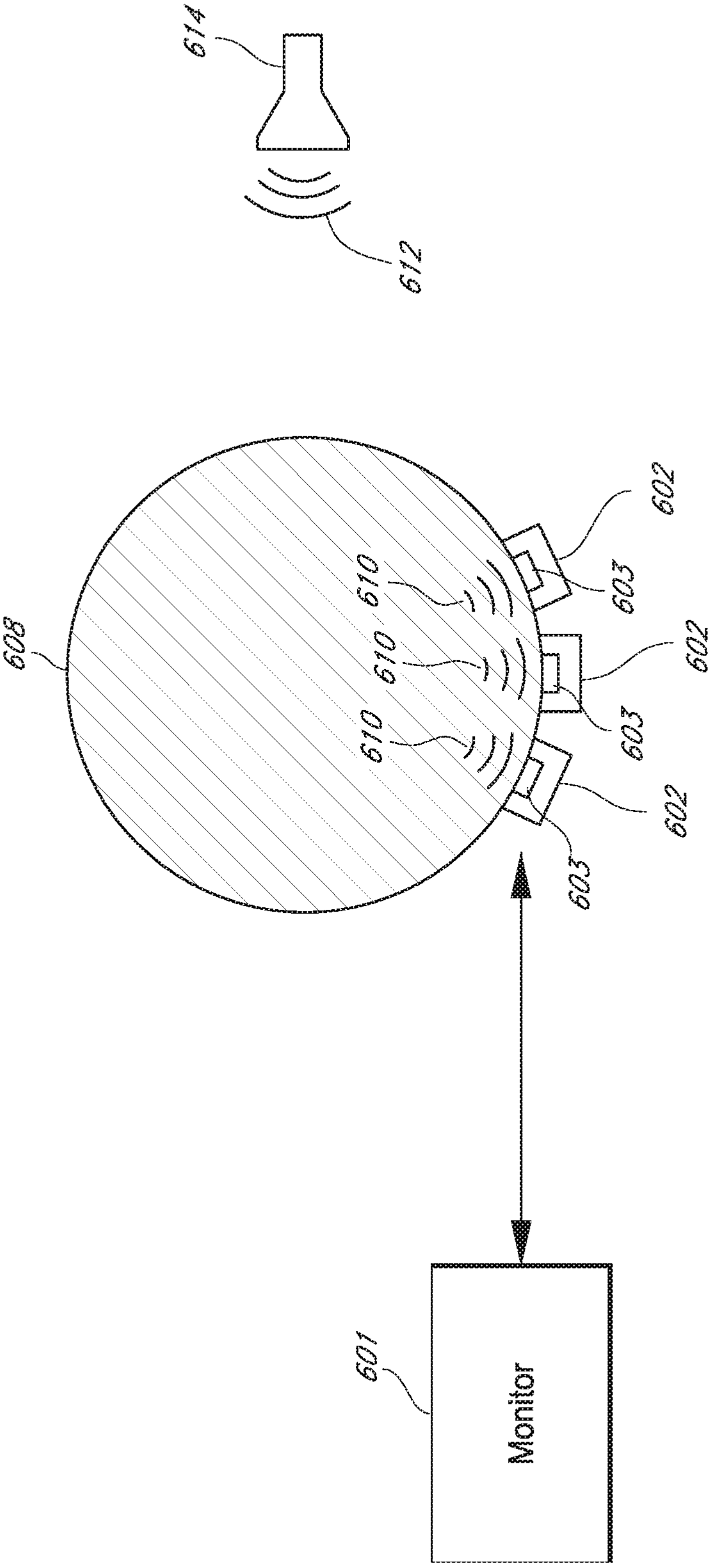
FIGS. 6A-B are top views of embodiments in which a plurality of sensors are attached to a patient according to embodiments of the disclosure.

FIG. 6A is a top view of an embodiment in which a plurality of acoustic sensors 602 are attached to various locations spaced about a patient's neck 608. The illustrated configuration can be used to generate a noise-reduced acoustical signal. Signals from the sensors 602 are communicated to a physiological monitor 601, which generates the noise reduced signal. In the example embodiment, first, second, and third acoustic sensors 602 comprising first, second and third sensing elements 603, are used. Other numbers of sensors (e.g., 2, 4, 5, or more) can be used in other configurations.

In general, the acoustic vibrations detected by the sensing elements 603 (e.g., a piezoelectric element) of the sensors 601 include bodily acoustic sounds 610 indicative of physiological parameters (e.g., breathing sounds indicative of respiratory rate, heart sounds, etc.). Additionally, the sensing elements 603 may detect acoustic vibrations 612 from environmental noise (sometimes referred to as ambient noise) emanating from one or more noise sources 614. As a result, the each of the individual sensing elements 603 will produce an electrical signal indicative of detected acoustic vibrations. Each electrical signal will therefore include a physiological sound component representative of the physiological parameter and a noise sound component representative of environmental and/or other noise.

In some embodiments, the acoustic noise sounds 612 include acoustic signals that do not emanate from the patient, but are detected by the sensors 602. For example, the noise sounds 612 may include noise from an external noise source 614, such as electronics (e.g., computers, medical equipment, motors, pumps, fans, alarms, or other electronics, etc.), noise from other people such as visiting family members and medical personnel in the vicinity of the patient, vehicle noise (e.g., in an ambulance), etc. In some embodiments, the noise sounds 612 include acoustic sounds coming from the patient that are not indicative of measured physiological parameters. Such sounds may include patient speech, coughing, etc.

The signal-to-noise ratio of the sensor signals is generally reduced due to the presence of the noise sounds 612. In some circumstances, a reduced signal-to-noise ratio can make it difficult to distinguish the physiological sound components of the signal from the noise components to provide accurate measurements. In certain embodiments, signals from the plurality of sensors 602 indicative of the noise sounds 612 and the bodily sounds 610 are advantageously processed (e.g., by the processor of the physiological monitor 601) so as to generate a noise reduced signal having a higher, improved signal to noise ratio than that of the individual sensor signals. Such techniques may operate to lower the ambient acoustical noise level and/or provide the sensor system with improved noise immunity.

In general, noise sounds 612 may include signals travelling at slower speeds and/or lower frequencies than the bodily acoustic sounds 610. For example, the noise sound 612 may generally travel through the air at the speed of sound, about 343 meters per second in some circumstances. As such, although the sensors 602 are spaced from each other, the noise sounds 612 generally arrive at the sensors 602 in phase or substantially in phase. For example, noise sounds 612 arriving at one of the sensors 602 arrives at substantially the same time, or relatively close to the same time as the noise sounds 612 arrive at the other sensors 602, and/or arrive in the same or substantially the same phase relationship.

The bodily sounds 610, on the other hand, generally travel at increased speeds and/or at higher frequencies than the noise sounds 612. In one embodiment, the bodily sounds 610 travel at about 1500 m/s through the patient's body. Because the bodily sounds 610 travel at an increased speed, the physical separation of the sensors 602 causes the bodily sounds 610 to arrive at the sensors 601 out of phase or substantially out of phase with one another. For example, the bodily sounds 610 may arrive at one of the sensors 602 at a significantly different time than the noise arriving at the other two sensors 602. In one embodiment, the bodily sounds 610 arrive at the sensors 602 significantly more out of phase, with significantly more time of arrival difference and/or phase difference between the sensors 602 than the noise sounds 612.

In certain embodiments, the sensor system advantageously utilizes the knowledge of the phase relationship between the noise sounds 612 arriving at the plurality of sensors 602 as compared to the phase relationship between the bodily sounds 610 arriving at the plurality of sensors 602 so as to generate a reduced noise signal. For example, the monitor of the sensor system may receive signals including both the noise sound 612 components and the bodily sound 610 components detected by the sensors 602. The system can operate to generate a noise reduced signal having a higher, improved signal to noise ratio than that of the signals from the individual sensor signals. For example, the noise reduction module may employ a cross-correlation technique in generating the noise reduced signal. This general noise reduction process may sometimes be referred to as a common mode rejection technique because components of each of the acoustic signals received by the sensors that were in-phase, or "common" (the noise sounds 612) are generally reduced or "rejected."

In one embodiment, the sensor system is configured to shift the signals from one or more of the sensors 602 with respect to the other sensor 602 signals, shifting the bodily sound components 610 of the sensor 602 signals in phase. The noise sound 612 components, on the other hand, are shifted out of phase with respect to one another. The shifted and un-shifted signals can be combined (e.g., summed together) to form a noise reduced signal.

Because the bodily sound components 610 are shifted to be in phase, they generally constructively interfere or otherwise combine in an additive manner. Moreover, the sensor 602 signals may be combined in an additive manner because the bodily sound components 610 may be coherent or substantially coherent relationship with respect to one another.

On the other hand, because the noise components 612 are shifted out of phase, they do not constructively interfere. For example, the noise components may destructively interfere or otherwise be combined in a non-additive manner. Moreover, the sensor 602 signals may combine in a non-additive manner because the noise sound components 612 may be in a non-coherent or substantially non-coherent relationship with respect to one another. As a result, the bodily sound components 610 of the noise reduced signal are increased relative to the noise signal components 612, thereby improving the signal to noise ratio of the noise reduced as signal as compared to the sensor 602 signals.

Figure 6B:
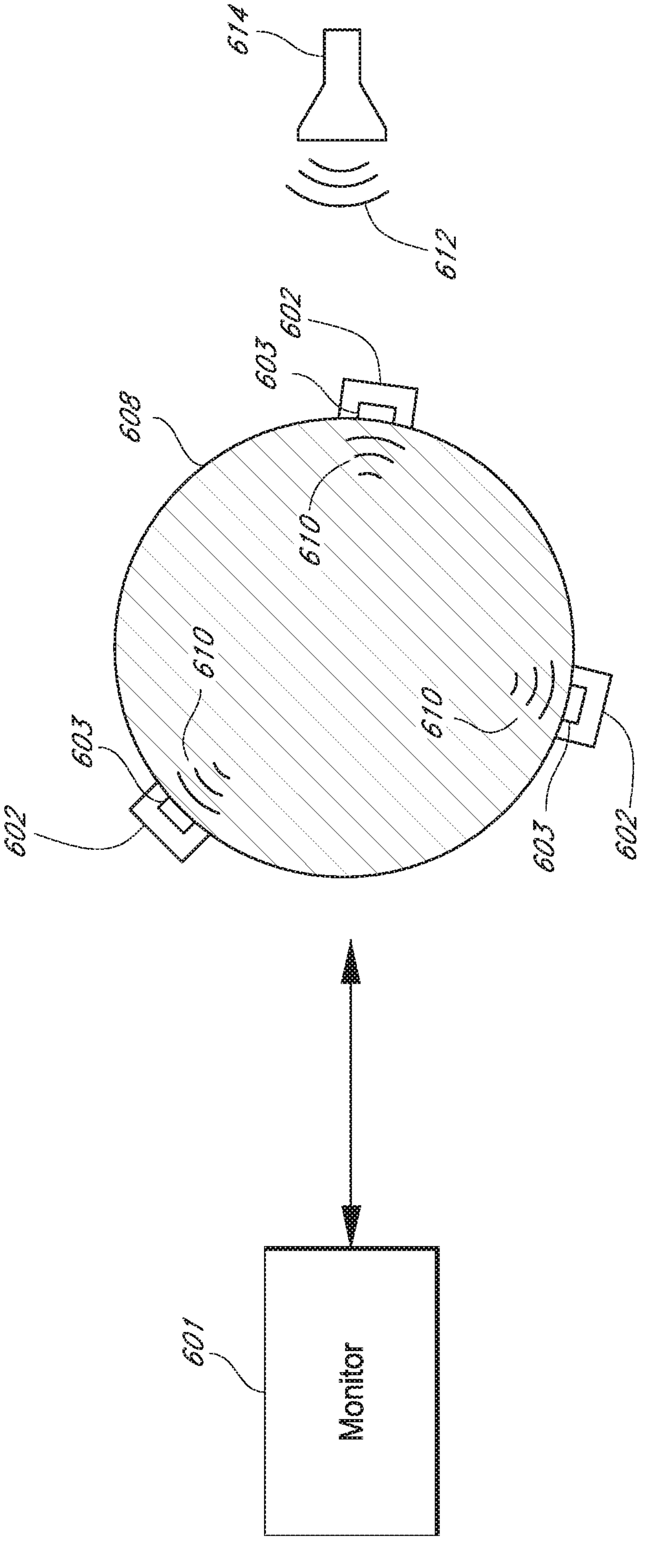

FIG. 6B is a top view of an embodiment in which a plurality of sensors 602 are spaced relatively far apart from one another. Such spatial separation can introduce more drastic differences in the phase relationship and/or signal intensity between the bodily sound components 610 of the signals.

Referring again to FIG. 6A, the plurality of sensors 602 positioned relatively closer together on the patient's neck 608 than in the embodiment of FIG. 6B. In one embodiment, the sensors 602 are coupled to a single attachment element and attached to the patient generally as a group. In contrast to the arrangement of FIG. 6B, the arrangement of FIG. 6A does not involve relatively long cables between the sensors 602. As such, signal noise and/or bulk which may be introduced by the use of such cables is avoided. In one embodiment, the sensors 602 comprise a plurality of sensing elements within a single sensor package (e.g., attached to a single sensor frame or support). Generally, any configuration having some physical separation of the sensing elements 603 may be compatible with certain embodiments described herein.

In certain embodiments, one or more of the plurality of sensors 602 includes an electrical shielding barrier such as those described above and in the Appendix. The multi-sensor noise reduction technique can operate in conjunction with electrical shielding barriers to improve overall noise reduction. For example, the techniques may combine synergistically to increase the signal-to-noise ratio, lower the noise floor, and/or improve the noise immunity of the system. In certain embodiments, the shielding barrier can reduce a first type of noise, while the noise reduction module 607 reduces a second type of noise. In one embodiment, the shielding barriers primarily reduce electrical interference (e.g., from external static electrical fields and electromagnetic fields) incident on the sensors while the noise reduction module 607 reduces acoustical noise.

Figure 7:
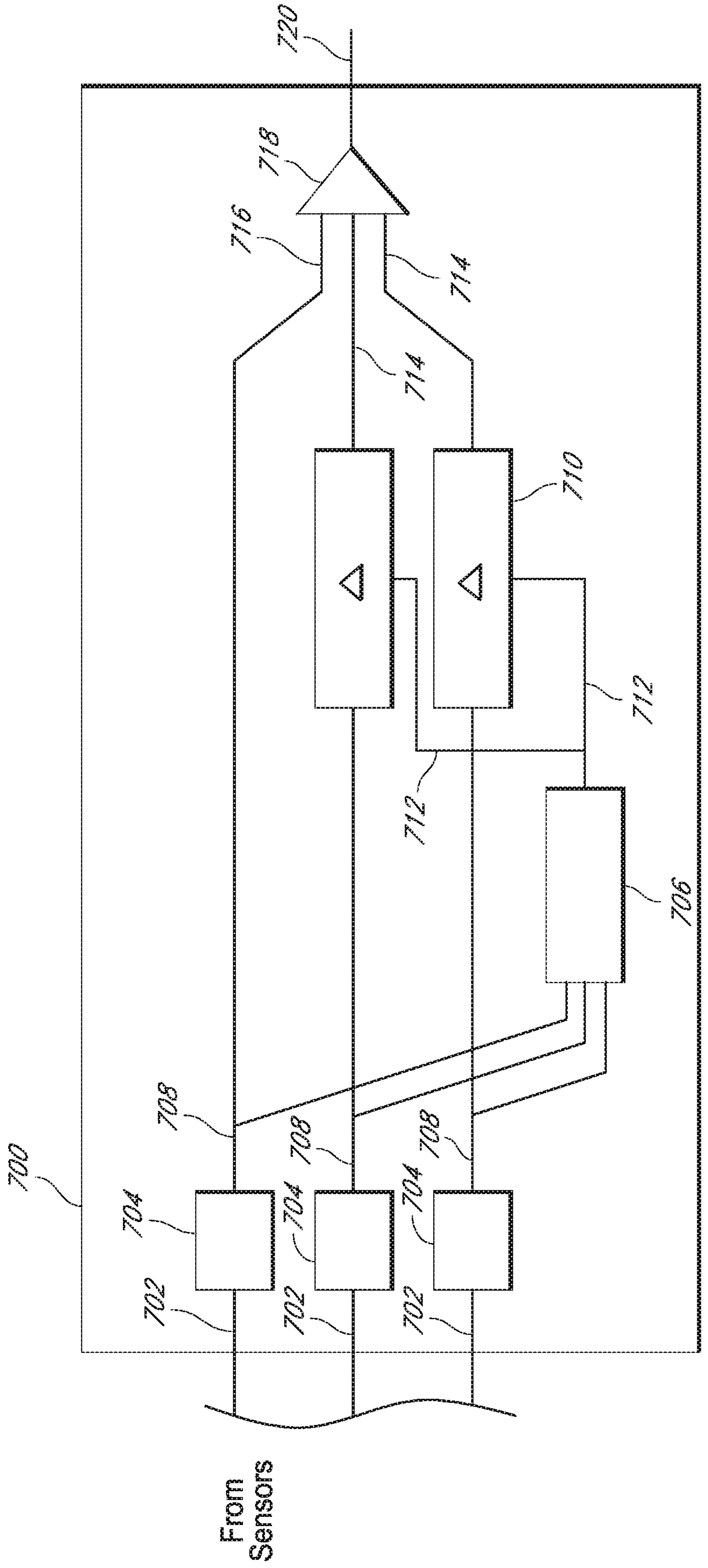
FIG. 7 is a block diagram illustrating a noise reduction module configured to process signals from multiple sensors according to embodiments of the disclosure.

FIG. 7 is a block diagram illustrating a noise reduction module 700 employing a cross-correlation technique to process a plurality of signals 702 from a plurality of sensors according to embodiments of the disclosure. The noise reduction module 700 outputs a noise reduced signal 720 advantageously having a lower signal-to-noise ratio than any of the signals 702 from the sensors. The noise reduction module 700 may be the noise reduction module 307 described with respect to FIG. 3, or some other noise reduction module. Additionally, the noise reduction module 700 may be compatible with the embodiments described with respect to FIG. 6A and/or 6B.

The noise reduction module 700 can include front end componentry 704 configured to condition the analog electrical signals 702 received from the acoustic sensors for processing. For example, the front end componentry 704 of one embodiment comprises a preamplifier, filter (e.g., high pass filter), amplifier, and/or analog to digital converter. In other embodiments, other circuitry may be provided in addition to or instead of these circuit components.

A cross-correlation module 706 receives the conditioned signals 708 and is configured to calculate a cross correlation of the signals 708. For example, the cross-correlation module 708 may generate a measure of the similarity of the signals 708 from sensors as a function of a time-lag applied to one of the signals. The cross-correlation calculation is sometimes referred to as a sliding dot product or inner product of the signals 708, for example.

The cross-correlation module 706 of certain embodiments shifts one or more of the signals 708 across one or more of the other signals in time and multiplies the shifted and un-shifted signals 708 together. Based on this shifting and multiplying operation, the cross-correlation module 706 can determine the value of time shift at which the multiplication of the signals is at a maximum value, relatively close to a maximum value, or at a relatively large value. This point may be referred sometimes to as the point of maximum energy or correlation between the signals 708.

As discussed, measurement signals 708 from the plurality of sensors can include both components indicative of bodily sounds and components indicative of noise, such as environmental noise. The bodily sound components of each of the signals 708 are generally out-of-phase with respect to each other. In contrast, the noise sound components of each of the signals 708 are generally in-phase with respect to each other.

Because the bodily sound signal components are relatively large in amplitude in relation to the environmental noise components, the point of maximum energy determined by the correlation module 706 corresponds to a shift amount at which the signals 708 have been synchronized, or shifted to be "in-phase" with one another in time.

Additionally, the shift amount corresponding to the point of maximum energy will shift the noise components of the signals 708, which were originally in phase with respect one another, to be out of phase.

The noise reduction module 700 can advantageously be configured to shift one of the sensor signals 708 from one of the sensors with respect to the signal 708 from the other sensor so as to place the bodily signal components of the two signals in phase, thereby also shifting the noise signal components out of phase. The shifted and un-shifted signals can be combined (e.g., summed together) to form a noise reduced signal.

For example, the cross-correlation module 706 outputs a plurality of shift signals 712 indicative of the shift amount corresponding to the point of maximum energy between the signals 708. In the illustrated embodiment, the signal 716 from one of the sensors is used as a reference and is therefore not shifted. Delay modules 710 are configured to delay one or more of the signals 708 according to the shift signals 712 to generate time-shifted signals 714 corresponding to time-shifted versions of one or more of the sensor signals 708. An output module 718 generates a noise-reduced signal 720. For example, the output module 718 may implement a summing function which adds together the time shifted signals 714 with the un-shifted signal 716.

In some configurations, the delay amount and shift signal 712 are calculated periodically or generally continuously so that potential changes in the phase relationships between the components of the signals 708 can be dynamically or adaptively accounted for. For example, in some cases, the phase relationship between bodily sound components of the signals 708 and the noise components of the signals 708 may change when a patient's respiratory rate increases dramatically, when new noise sources are introduced into the monitoring environment, or for other reasons. Periodically adjusting the delay amount and corresponding shift value 712 to account for such changes may improve monitoring accuracy. In one embodiment, the cross-correlation module 706 calculates the delay amount and corresponding shift signal 712 once at the beginning of a measurement cycle.

In various embodiments, other techniques or variations of the techniques described above may be used to find the point of maximum energy between the signals and corresponding appropriate delay amount. For example, the noise rejection module may employ a "shift and add" approach may be used instead of a "shift and multiply" approach generally employed by the cross-correlation module 706. In such an embodiment, the time-shifted signal may be added to the other signal as it is shifted instead of being multiplied with the other signal. Other techniques may include variations of cross-correlation or generally any techniques capable of finding points of similarity or maximum energy between two signals.

FIG. 7 illustrates an embodiment including three sensors and three associated sensor signals 702. In other embodiments, the sensor system includes two sensors or more than three sensors and the noise reduction module 700 is configured to receive and process a corresponding number of sensor signals. In such embodiments, for example, the delay module 710 can be configured to delay more than two of the signals 708 so as to place the bodily sound components of the signals 708 in phase, and the noise components of the signals 708 out of phase. In the general case where there are n signals and one signal is used as a reference signal, n−1 of the signals are delayed with respect to the reference signal.

The various components of the noise reduction module 700 may be implemented in hardware, software, or a combination thereof. In one embodiment, the front-end componentry is implemented in analog circuitry while the cross-correlation module 706 and the delay module 708 are implemented in software running on a processor of a physiological monitor.

Figure 8:
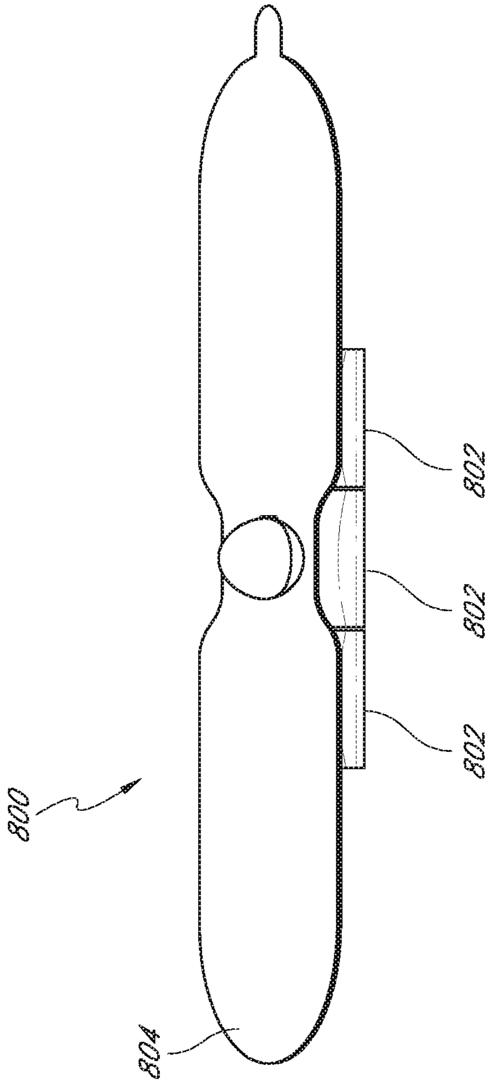
FIG. 8 is a perspective view of a multi-sensor arrangement including multiple sensor assemblies adjacent to one another according to embodiments of the disclosure.

FIG. 8 is a perspective view of a multi-sensor arrangement 800 including multiple sensor assemblies 802 adjacent to one another according to embodiments of the disclosure. The multi-sensor arrangement 800 may be configured to provide a noise reduced signal using signals from the individual sensor assemblies 802 according to embodiments described herein. The individual sensors 802 may be any of the sensors described herein such as one of the sensor 201 of FIG. 2, the sensors 312 of FIG. 3, the sensors 602 of FIGS. 6A-6B, or some other sensors.

In one embodiment, the signals from each sensor are communicated over separate conductors via the cable 804. In another embodiment, the signals from the multiple sensors 802 are communicated over the same conductor or conductors and the signals from the multiple sensors 802 are multiplexed or interleaved for communication between each of the sensors 802 and the monitor, or are otherwise sent over the single lead or wire. In other embodiments, the sensors 802 may not be chained together or otherwise connected, and separate cables connect the individual sensors 802 to the monitor.

In certain embodiments, the cable 804 may include one or more patient anchors such as those described herein and in the Appendix for securing the cable to the patient and decoupling the attachment between the sensors 802 and the patient from movement of the cable due to movements such as accidental yanking or jerking. In one embodiment, one patient anchor is positioned in the region of the cable between the monitor and the first sensor 802 in the chain, and other patient anchors are positioned in the regions between each of the sensors 802 in the chain. Such arrangements can reduce accidental sensor disconnection.

Figure 9:
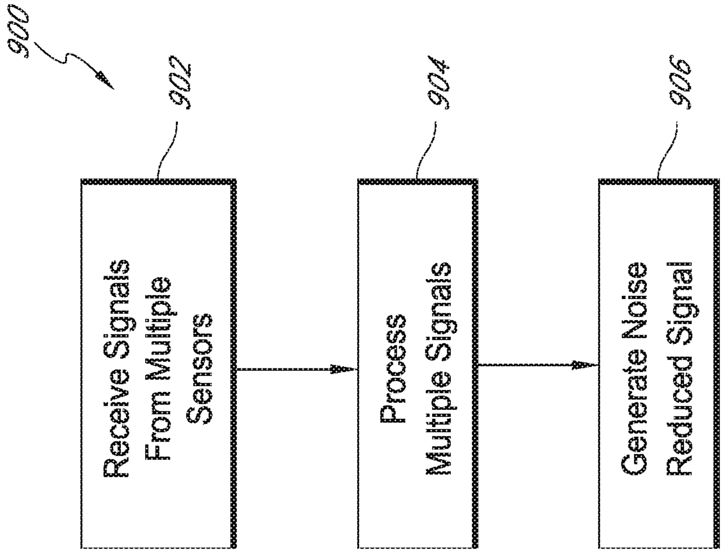
FIG. 9 is a flow chart illustrating a method of processing signals from a plurality of sensors in accordance with embodiments of the disclosure.
Figure 10A:
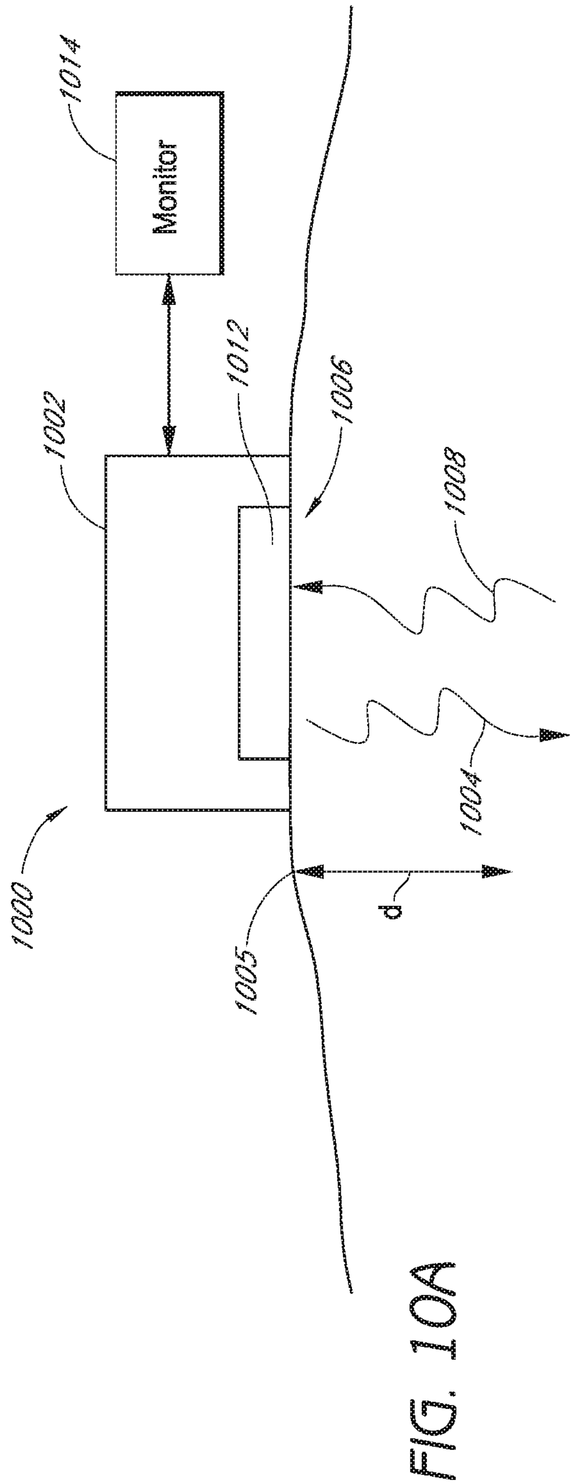
FIG. 10A-B schematically illustrate sensor systems including an active acoustic sensors configured to both transmit acoustic vibrations into a measurement site and receive acoustic vibrations from the measurement site.

FIG. 9 is a flow chart illustrating a method 900 of processing signals from a plurality of sensors in accordance with embodiments of the disclosure. At step 902, the method 900 receives signals from multiple acoustic sensors attached to a patient at a plurality of measurement sites. Any number of acoustic sensors may be attached to the patient. For example, 2, 3, 4, 5 or more sensors may be applied in certain embodiments.

The multiple sensors may be arranged in and be compatible with any of the configurations described herein, such the configurations of FIGS. 6A and 6B. The method 900 may further be compatible with any of the noise reduction embodiments described herein. For example, the method 900 may be compatible with and perform the noise reduction function of the noise reduction modules 300, 500 of FIGS. 3 and/or 7.

As discussed herein with respect to FIGS. 6A-8, the received signals may include bodily sound components which are out of phase with respect to the bodily sound components of the signals from the other sensors and noise components which are in phase with respect to the noise components of the signals from the other sensors.

At step 904, the method 900 processes the multiple signals. For example, the method 900 may perform a cross-correlation operation so as to detect a time shift of the bodily signal components of the signals from the multiple sensors with respect to each other. In other embodiments, the method 900 may perform some other cross-correlation function, or some other technique to identify a time shift between bodily sound components of the signals.

At step 906, in one embodiment, the method 900 generates a noise reduced signal. For example, the method 900 may shift one or more of the sensor signals so as to generally line up the bodily sound components of the sensor signals with respect to the bodily sound components of the signals from the other sensors. The shift may also advantageously move the noise components of the sensor signals into an out of phase relationship with respect to the noise components form the other sensors.

At step 906, the method 900 further combines the shifted and un-shifted sensor signals so as to generate a noise reduced signal. For example, the bodily sound components of the signals from the multiple sensors may constructively combine or interfere, while the noise sound components do not, resulting in a signal having an improved signal to noise ratio.

Active Sensing

FIG. 10A schematically illustrates a sensor system 1000 including an acoustic sensor 1002 configured to both transmit acoustic vibrations 1004 into a measurement site 1006, and receive and sense acoustic vibrations 1008 from the measurement site. In such embodiments, the sensor 1002 can be used for other beneficial purposes in addition to measuring physiological parameters. For example, an acoustic signal 1004 can be transmitted into the skin of the patient 1005 at a measurement site 1006 and the acoustic response signal 1008 from the measurement site 1006 can be detected and processed so as to characterize a measurement site parameter. Such parameters can include tissue type at the measurement site 1006, the integrity of the mechanical connection between the sensor and measurement site 1006, etc.

Such information can advantageously be used for sensor calibration, alerting medical personnel (e.g., to probe-off conditions), and the like. A sensor 1002 having transmission and reception functionality may sometimes be referred to as an "active" sensor because it is capable of actively sending a signal into the measurement site 1006 to generates a response 1008, as well as passively receiving acoustic vibrations (e.g., from bodily sounds).

A sensing element 1012 of the sensor 1002 may be any of the sensing elements described herein, or some other sensing element 1012. In one embodiment, the sensing element 1012 may include a piezoelectric device such as a piezoelectric membrane. As described herein, piezoelectric membranes may be configured to convert mechanical deformations, such as those caused by acoustic vibrations coming from the patient's skin at a measurement site, into an electric voltage.

Additionally, in certain embodiments, a voltage may be applied to the piezoelectric membrane so as to actively deform the membrane. Modulation of the voltage applied to the membrane can thus cause it to vibrate, thereby emitting acoustic vibrations 1004 into the measurement site 1006. For piezoelectric sensing elements 1012, electrical signal values corresponding to received vibrations of a certain intensity can be much lower than the electrical signal values used to actively vibrate the sensor at a similar intensity. Thus, the sensing element 1012 may be characterized as lacking reciprocity with respect to transmission and reception of acoustic waves. To address the lack of reciprocity, a relatively high voltage driver may be used to drive the sensing element 1012 and generate the emitted vibrations 1004.

Although the arrows representing the emitted and detected acoustic vibrations 1004, 1008 are shown as leaving from different sides of the sensing element 1012, this is for the purposes of illustration only and is not limiting. Indeed, the emitted and detected acoustic vibrations 1004, 1008 may be transmitted and received from the same sensing element 1012 portion.

Acoustic vibrations 1008 may be generated from the measurement site 1006 (e.g., from the patient's skin) in response to the vibrations 1004 transmitted into the measurement site by the sensor 1002. The acoustic vibrations 1008 are received by the sensing element 1012 and may then be converted into an electrical signal which is then processed by the sensor system 1000. For example, a processor in the monitor 1014 may process the acoustic response 1008.

For example, the monitor 1014 may process a received signal including both (1) the acoustic response signal 1008 generated in response to the transmitted signal 1008 and (2) acoustic vibrations from bodily noises (e.g., respiratory rate, etc.) not associated with the acoustic response signal 1008. In certain embodiments, modulation of the driver signal is used to distinguish the signals. For example, in one embodiment, the transmitted signal includes bursts with a specific embedded pattern or signature. A lock filter is then used to identify only received signals including the pattern or signature will be identified as signals 1008 generated in response to the transmitted signal 1004. In other configurations, various forms of frequency or amplitude modulation may be employed.

In certain embodiments, instead of using modulation, a baseline reading is taken of the bodily noises (e.g., the patient's breathing) not associated with the response signal 1008. The baseline can then be subtracted from the received signal so that the sensor system can distinguish the normal bodily noises from the acoustic response signal 1008. In other embodiments, a filter (e.g., a high-pass, low-pass or band-pass filter) or some other mechanism may be used instead of, or in addition to the baseline approach to distinguish the acoustic response signal 1008.

Because various measurement sites will have certain characteristic acoustic responses 1008, the acoustic response 1008 can beneficially be used to determine a parameter (e.g., to characterize the measurement site 1006 and/or the connection between the measurement site 1006 and the sensor 1002). The information can then be intelligently used by the sensor system 1000. For example, the sensor system 1000 may be use the information to calibrate the sensor, provide diagnosis, etc.

In one embodiment, the acoustic response 1008 is processed to identify whether or not the measurement site 1008 the sensor is attached to a measurement site. For example, the sensor system 1000 may determine whether or not the measurement site 1008 is appropriately attached to human skin. If not, the system 1000 may provide an alarm or other probe-off indication. In certain embodiments, based on the acoustic response 1008, the sensor system 1000 may enable or disable sensor 1002 operation. The sensor system 1000 may disable the sensor 1002 in a probe-off situation, for instance. In other embodiments, the sensor system 1000 may determine a probe-off situation by detecting whether or not the sensor 1002 is attached to a solid object.

The system 1000 may determine the integrity of the connection between the sensor 1002 and the measurement site 1006 in certain embodiments. For example, given a known type of measurement site (e.g., skin), the total energy received in response to the acoustic vibrations 1004 may be indicative of the strength of the connection between the sensor 1002 and the measurement site 1006.

Such information may then be used to calibrate the sensor 1002, enable or disable the sensor 1002, or provide information to the user (e.g., communicate to the user that there is a weak sensor/measurement site connection). In an embodiment, if a relatively weak connection is detected, the system 1000 may increase the gain of the sensor 1002.

In other embodiments, the sensor system 1000 may provide detailed information regarding the measurement site. For example, the sensor system 100 may be able to characterize parameters such as tissue composition (e.g., fat and water percentage composition), tissue type, etc.

In processing the response signal 1008, the sensor system 1000 may, in certain embodiments, access a library of responses. For example, the system 1000 may compare the received response to entries in the library. In one embodiment, the response signal 1008 is compared to a series of previously recorded responses for various types of tissue (e.g., tissue of a particular region of the body, tissue having a particular composition, etc.).

In some embodiments, a library specific to the patient is generated and used for analyzing future response signals 1008. For example, in one embodiment acoustic responses 1008 are generated while the sensor 1002 is attached to various regions of a patient's body and the responses are stored in a library. Once the library is generated, future responses 1008 can be characterized by comparing the responses 1008 to those in the library.

Based on the comparison of the response signal 1008 with those recorded and stored in the library, various parameters such as the type of tissue, characteristic of the tissue, the integrity of the connection between the sensor and the measurement site, etc., may be determined. Such parameters may then be used by the system 1000 for beneficial purposes, such as for calibrating the sensor, providing diagnostic information, providing probe-off indications, etc.

The acoustic vibrations 1004 can be transmitted a depth d into the measurement site 1006 (e.g., a patient's skin). In certain embodiments, the acoustic vibrations 1004 may penetrate relatively deeply into the patient's skin, for example, allowing for improved parameter determination such as improved characterization of the measurement site. In other embodiments, the acoustic vibrations measure a response at the surface of the measurement site 1006. In some embodiments, the intensity or other parameter (e.g., frequency) of the transmitted acoustic signal 1004 can be controlled in order to adjust the level of penetration into the patient's skin 1005.

In certain embodiments, active sensing can be used for enhanced respiratory monitoring. For example, in one embodiment the sensor 1002 is configured to emit the transmitted signals 1004 to a depth sufficient to reach airway walls, the tissue walls that define the patient's respiratory airways. Airway walls are generally the surfaces that move from respiratory airflows, creating respiratory sounds. For example, the transmitted signal 1004 reaches the tracheal wall in one embodiment.

In such cases, the response signal 1008 is reflected off of the airway wall, received by the sensor 1002 and processed to sense the respiratory sounds of the patient. As described, the system filters out received signals other than the signals 1008 generated directly in response to the transmitted signal 1004 (e.g., using a signature and lock filter). Non-respiratory sound noise is removed. Additionally, distorting effects from the tissue that the reflected response signal 1008 travels through from the airway wall to the sensor is also removed.

As such, an active respiratory monitoring technique using the active sensor 1002 beneficially provides detection of respiratory sounds effectively at the source (the airway wall), providing highly accurate respiratory measurements. Moreover, respiratory sounds from precise locations in the patient's respiratory system may be targeted and detected using active respiratory sensing.

The active sensor functionality is periodically employed during sensor use in some embodiments. For example, in one embodiment, the transmitted acoustic signal 1004 is generated and the response 1008 is measured and processed at regular intervals. For example, the system 1000 may interrupt the normal sensor functionality of measuring acoustic vibrations indicative of various physiological parameters (e.g., respiratory rate, etc.) at regular intervals. During those intervals, the active sensor functionality described herein can be employed to determine a parameter (e.g., to detect probe-off, calibrate the sensor, etc.).

In one embodiment, the interval period is one second. Other intervals may include intervals from between 2 and 60 seconds, less than one second, or greater than 60 seconds. In some embodiments, the normal sensor functionality and the active sensor functionality are performed generally at the same time and the normal sensor functionality is not interrupted.

Figure 10B:
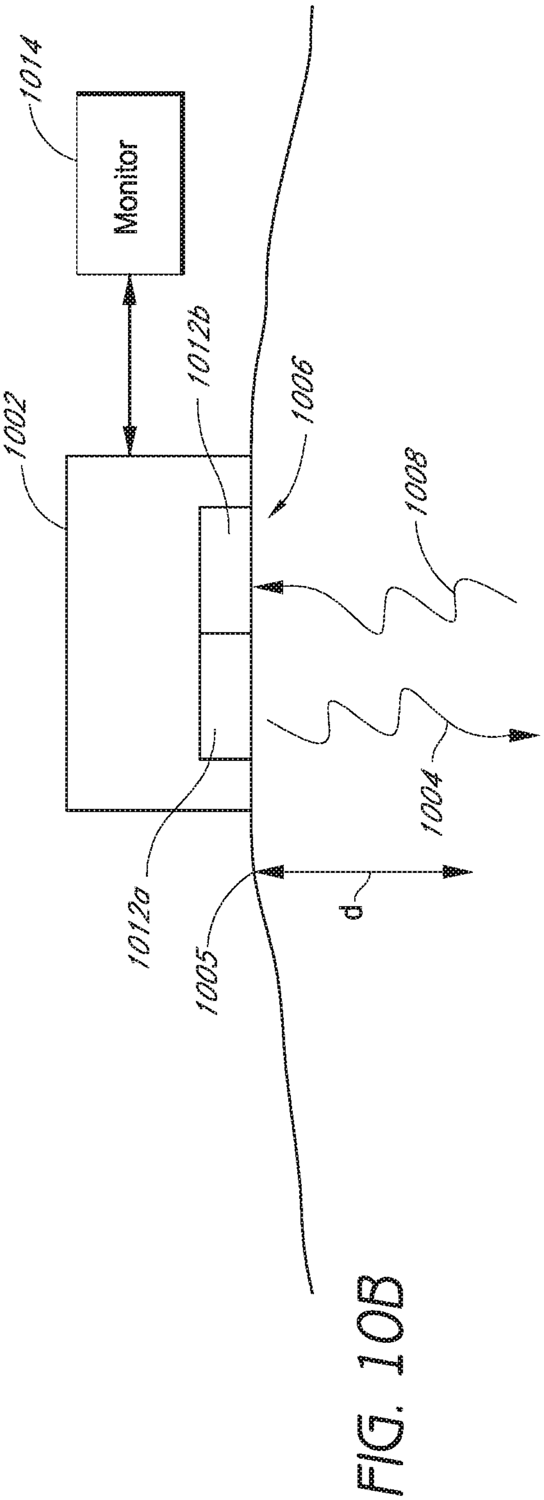
Figure 11:
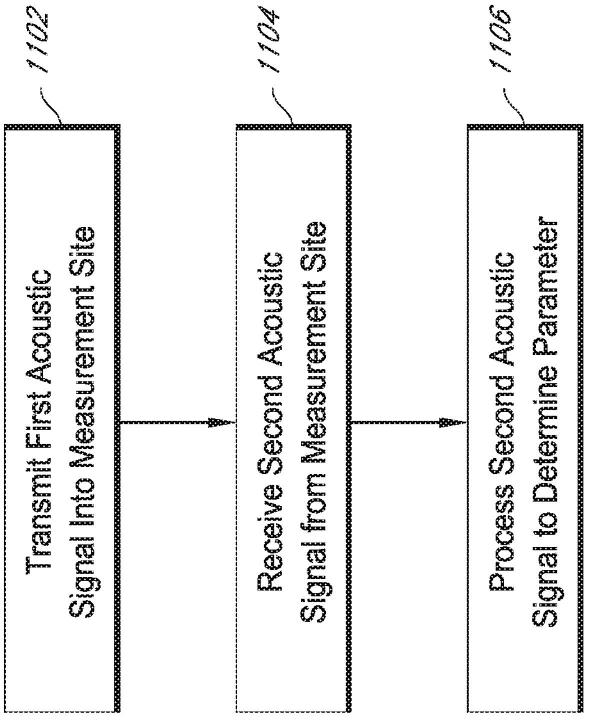
FIG. 11 is a flow chart illustrating a method of using an acoustic sensor in an active configuration.

As shown in FIG. 10B, more than one sensing element 1012 may be used in certain embodiments. For example, the sensor 1002 may include first and second sensing elements 1012*a*, 1012*b*. In one embodiment, the first sensing element 1012*a* is actuated to transmit the acoustic signal 1004 into the measurement site 1006, and the response signal 1008 received by the second sensing element 1012*b* is processed by the system 1000. Other embodiments may include more two sensing elements 1012, two or more separate sensors 1002, etc.

The processing of the acoustic response 1008 is described with respect to FIG. 10 as being implemented in the monitor 1014. In various other embodiments, the acoustic response 1008 may be processed, at least in part, in some other location in the sensor system 1000, such as on a processor of the sensor 1002, for example.

FIG. 11 is a flow chart illustrating a method 1100 of using an acoustic sensor in an active configuration. The acoustic sensor is generally capable of both transmitting acoustic signals into a measurement site of a patient and receiving acoustic signals from the measurement site so as to determine a parameter. For example, the acoustic sensor may be one of the acoustic sensors 1002 of FIGS. 10A-B, or may be some other acoustic sensor.

At step 1102, the method 1100 transmits a first acoustic signal into a measurement site with the sensor. For example, a voltage may be applied to a piezoelectric sensing element of the sensor so as to vibrate the sensing element and transmit acoustic sound waves into the measurement site.

At step 1104, the method 1100 receives a second acoustic signal from the measurement site. The second acoustic signal is generated in response to the transmitted signal. For example, certain tissues and other materials may generate characteristic acoustic signals in response to the first acoustic signal.

At step 1104, the method 1100 may also receive acoustic signals indicative of bodily or other noises not generated in response to the first acoustic signal. In such cases, the method 1100 may distinguish the second acoustic signal from the other sounds, such as by using a baseline, some type of filter, or a combination thereof, as described with respect to FIG. 10A-B above.

At step 1106, the method 1100 processes the second acoustic signal. For example, the method 1100 may be processed so as to determine one or parameters, such as to characterize the tissue, determine the integrity of the mechanical connection between the sensor and measurement site, or for other purposes. Such information can advantageously be used for sensor calibration, alerting medical personnel (e.g., to probe-off conditions), and the like.

Additional Example Sensor System

Figure 12:
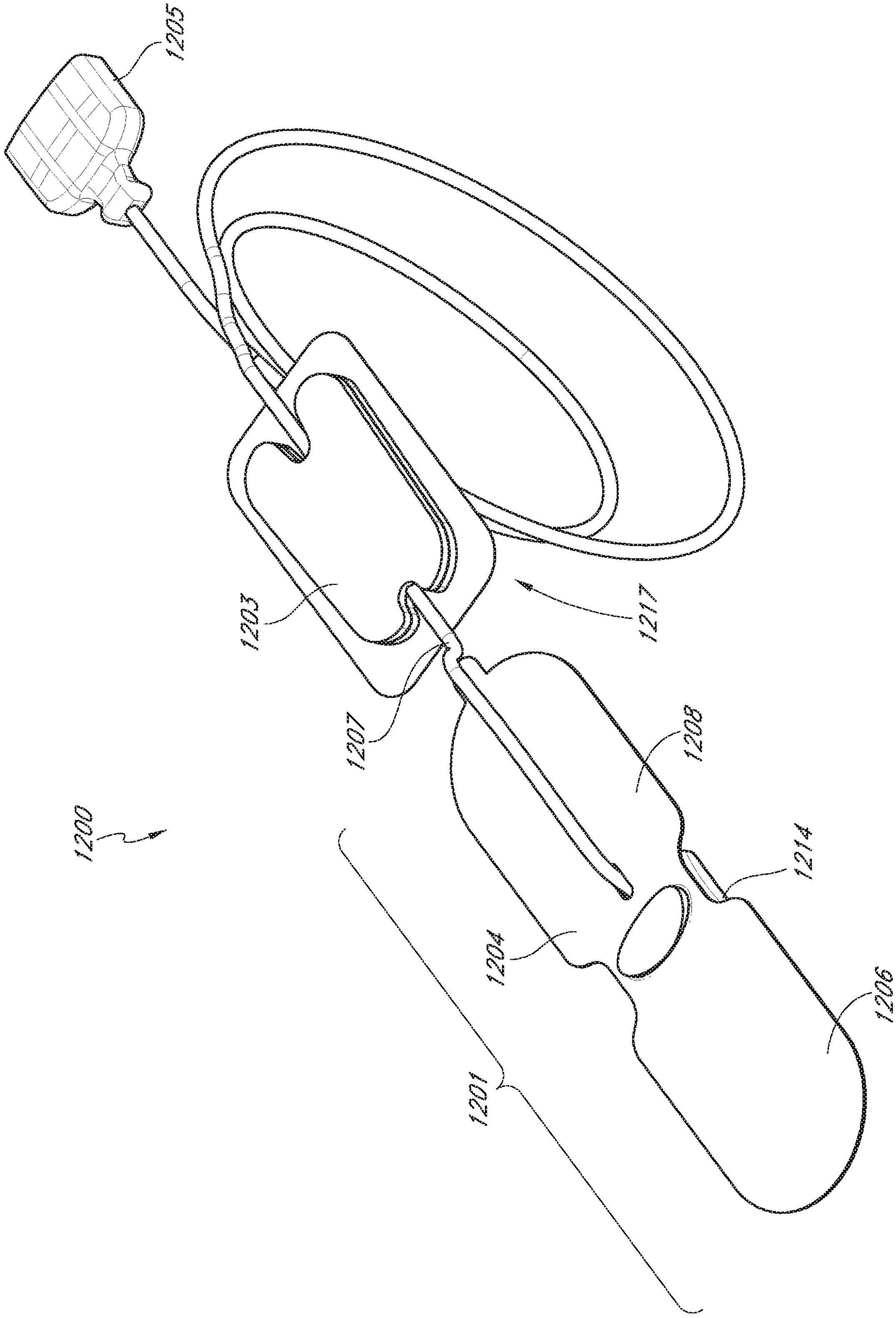
FIG. 12 is a top perspective view illustrating portions of another example sensor system in accordance with an embodiment of the disclosure.

FIG. 12 is a top perspective of a sensor system 1200 that includes a sensor 1201 suitable for use with any of the physiological monitors shown in FIGS. 1A-C and with various embodiments described herein. The sensor system 1200 also includes a cable 1207. The sensor 1201 includes an attachment element 1204 and an acoustic coupler 1214 enclosing various components of the sensor 1201. The cable 1207 of one embodiment includes a patient anchor 1203. The cable 1207 includes a connector 1205 removably attachable to a monitor connector (not shown) connectable to a physiological monitor (not shown) through another section of cable (not shown).

In various embodiments, not all of the components illustrated in FIG. 12 are included in the sensor system 1200. For example, in various embodiments, one or more of the patient anchor 1203 and the attachment element 1204 are not included. In one embodiment, for example, a bandage or tape is used instead of the attachment element 1204 to attach the sensor 1201 to a measurement site. Moreover, such bandages or tapes may be a variety of different shapes including generally elongate, circular and oval, for example.

The acoustic sensor 1201 of certain embodiments includes a sensing element (not shown), such as, for example, a piezoelectric device or other acoustic sensing device. The sensing element generates a voltage that is responsive to vibrations generated by the patient, and the sensor includes circuitry to transmit the voltage generated by the sensing element to a processor for processing. In an embodiment, the acoustic sensor 1201 includes circuitry for detecting and transmitting information related to biological sounds to a physiological monitor. These biological sounds may include heart, breathing, and/or digestive system sounds, in addition to many other physiological phenomena. The acoustic sensor 1201 in certain embodiments is a biological sound sensor, such as the sensors described herein. In some embodiments, the biological sound sensor is one of the sensors such as those described in the '883 Application, the '939 Application. In other embodiments, the acoustic sensor 1201 is a biological sound sensor such as those described in U.S. Pat. No. 6,661,161, which is incorporated by reference herein. Other embodiments include other suitable acoustic sensors. For example, in one embodiment, the sensor 1201 is configured to be attached to a patient and includes a sensing element configured to detect bodily sounds from a patient measurement site.

The sensing element may include a piezoelectric membrane, for example, and is supported by a support structure such as a generally rectangular support frame. The piezoelectric membrane is configured to vibrate in response to acoustic vibrations, which generates electrical signals indicative of the bodily sounds of the patient at the membranes poles. Example sensing elements compatible with embodiments disclosed herein are disclosed in the '939 Application. For example, sensing elements are described and/or shown in and described with respect to FIGS. 2A-3C and 6A-6E of the '939 Application.

The acoustic sensor 1201 may also include an electrical shielding barrier, providing for beneficial electrical shielding of a sensing element, such as a piezoelectric element of the sensor, from external electrical noises. The electrical shielding barrier can include one or more layers which form a Faraday cage around the piezoelectric element, for example, and which distribute external electrical noise substantially equally to first and second electrical poles of the piezoelectric sensing element. In addition, the shielding barrier flexibly conforms to the surface shape of the piezoelectric element as the surface shape of the piezoelectric element changes, thereby improving the shielding and sensor performance. Shielding barriers compatible with embodiments disclosed herein are disclosed in the Appendix. For example, such shielding barriers are shown in and described with respect to FIGS. 2B-2E and 6B-6E of the '939 Application.

The sensor 1201 of the illustrated embodiment includes an acoustic coupler 1214 which in one embodiment envelops or at least partially covers some or all of other components of the sensor 1201. The bottom of the acoustic coupler 1214 includes a contact portion 1216 which is brought into contact with the skin of the patient. The acoustic coupler 1214 is configured to transmit bodily sound waves to the sensing element and improves the coupling between the source of the signal to be measured by the sensor (e.g., the patient's skin) and the sensing element. Improved coupling provides an increased signal to noise ratio. The acoustic coupler 1214 of one embodiment includes a bump positioned to apply pressure to the sensing element so as to bias the sensing element in tension. Example acoustic couplers compatible with embodiments described herein shown in and described with respect to FIGS. 2A-2E, 4, 5A-5B and 6A-6E of the '939 Application.

The attachment element 1204 includes first and second elongate portions 1206, 1208. The first and second elongate portions 1206, 1208 can include patient adhesive (e.g., in some embodiments, tape, glue, a suction device, etc.) attached to a resilient backbone (not shown). The adhesive on the elongate portions 1206, 1208 can be used to secure the sensor 1201 to a patient's skin. The attachment element 1204 can beneficially bias the sensor 1201 in tension against the patient's skin and reduce stress on the connection between the patient adhesive and the skin. A removable backing can be provided with the patient adhesive to protect the adhesive surface prior to affixing to a patient's skin. Example of attachment elements compatible with embodiments described herein are disclosed in the Appendix. Such attachment elements are shown in and described with respect to FIGS. 2A, 9A-9D, and 10 of the '939 Application, for example.

The sensor cable 1207 is electrically coupled to the sensor 1201 via a printed circuit board ("PCB") (not shown) residing in the sensor 1201. Through this contact, electrical signals are communicated from the multi-parameter sensor 1201 to the physiological monitor through the may advantageously secures the sensor to the patient at a point between the ends of the sensor cable 1207. The patient anchor 1203 attached to the cable 1207 advantageously secures the sensor to the patient at a point between the ends of the cable 1207. Securing the cable 1207 to the patient can decouple movement of the cable 1207 due to various movements such as accidental yanking or jerking on the cable 1207 or movement of the patient. Such decoupling advantageously reduces the noise detected by the sensor when the cable 1207 is moved. Patient anchors compatible with embodiments described herein are shown in and described with respect to FIGS. 2A, 11A-B and 12 of the patent application entitled, "ACOUSTIC SENSOR ASSEMBLY", for example.

Terminology/Additional Embodiments

The modules described herein of certain embodiments may be implemented as software modules, hardware modules, or a combination thereof. In general, the word "module," as used herein, can refer to logic embodied in hardware or firmware or to a collection of software instructions executable on a processor. Additionally, the modules or components thereof may be implemented in analog circuitry in some embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensing system, the acoustic sensing system comprising:

an acoustic sensor configured to generate an initial signal in response to detecting acoustic vibrations associated with a patient; and a processing circuitry configured to:

receive the initial signal; and determine a first portion of the initial signal that is above a predetermined threshold amount, wherein the predetermined threshold amount is greater than a level corresponding to breathing sounds and less than a saturation level of a preamplifier; and compress the first portion of the initial signal according to a first compression scheme selected from a plurality of dynamic range compression schemes to generate a first compressed portion, the first compression scheme selected to increase a dynamic range of front-end circuitry of the acoustic sensor, wherein a second portion of the initial signal that is below the predetermined threshold amount is not compressed;

wherein the processing circuitry is configured to generate a modified sensor signal comprising the first compressed portion and the not compressed second portion; and wherein the front-end circuitry comprises the preamplifier and is configured to receive the modified sensor signal at an input of the preamplifier instead of receiving the initial signal.

2. The acoustic sensing system of claim 1, wherein the first portion of the initial signal corresponds to a sound that is higher in volume than a breathing sound.

3. The acoustic sensing system of claim 1, further comprising a decompression module configured to remove distortion effects introduced by the compression.

4. The acoustic sensing system of claim 1, wherein the front-end circuitry is configured to produce an amplified signal based on the first portion and the second portion.

5. The acoustic sensing system of claim 1, wherein the second portion corresponds to a sound that is equal to or lower in volume than a breathing sound.

6. The acoustic sensing system of claim 1, wherein the front-end circuitry comprises the preamplifier.

7. The acoustic sensing system of claim 1, wherein the first compression scheme comprises executing a logarithmic function.

8. The acoustic sensing system of claim 1, wherein the first compression scheme comprises executing a linear function.

9. The acoustic sensing system of claim 8, wherein the linear function comprises a piece-wise linear function.

* * * * *